United States Patent
Ortiz Alemán et al.

(10) Patent No.: US 7,496,450 B2
(45) Date of Patent: Feb. 24, 2009

(54) METHOD FOR IMAGING MULTIPHASE FLOW USING ELECTRICAL CAPACITANCE TOMOGRAPHY

(75) Inventors: José Carlos Ortiz Alemán, Eje Central Norte Lázaro Cárdenas (MX); Roland Martin, Eje Central Norte Lázaro Cárdenas (MX); José Carlos Gamio Roffé, Eje Central Norte Lázaro Cárdenas (MX)

(73) Assignee: Instituto Mexicano del Petroleo, Mexico, D.F. (MX)

( * ) Notice: Subject to any disclaimer, the term of this patent is extended or adjusted under 35 U.S.C. 154(b) by 0 days.

(21) Appl. No.: 10/568,814

(22) PCT Filed: Aug. 22, 2003

(86) PCT No.: PCT/MX03/00067

§ 371 (c)(1),
(2), (4) Date: Sep. 6, 2006

(87) PCT Pub. No.: WO2005/019779

PCT Pub. Date: Mar. 3, 2005

(65) Prior Publication Data

US 2007/0133746 A1 Jun. 14, 2007

(51) Int. Cl.
*G06F 19/00* (2006.01)
(52) U.S. Cl. .......................................... 702/6
(58) Field of Classification Search .............. 702/2, 702/6, 12, 13
See application file for complete search history.

(56) References Cited

U.S. PATENT DOCUMENTS 5,255,345 A    10/1993   Shaefer
5,984,023 A *  11/1999   Sharma et al. ............... 175/50
6,434,265 B1 * 8/2002    Xiong et al. ................. 382/154
6,549,651 B2 * 4/2003    Xiong et al. ................. 382/154
6,577,700 B1   6/2003    Fan et al.
6,775,405 B1 * 8/2004    Zhu .............................. 382/154

(Continued)

FOREIGN PATENT DOCUMENTS

EP           0 326 266           8/1989

(Continued)

OTHER PUBLICATIONS

Cruz-Atienza V. M. Inversion global con algoritmos geneticos y cristalizacion simulada aplicada a funciones de receptor: modelos estructurales de velocidades para la corteza en la Republica Mexicana. 1999, Tesis, Facultad de Ingenieria, UNAM.

(Continued)

*Primary Examiner*—Edward Raymond
(74) *Attorney, Agent, or Firm*—Roylance, Abrams, Berdo & Goodman, L.L.P.

(57) ABSTRACT

The invention relates to an image-reconstruction technique which is used to view multiphase flows using electrical capacitance tomography (ECT), which is based on non-linear heuristic global optimization methods involving simulated annealing and genetic algorithms. The inventive method consists in obtaining electrical capacitance data which are measured between electrodes positioned on the outer surface of pipeline, well or tank (electrically-insulating) containing fluids. The aforementioned data are dependent on the distribution of the fluids inside the pipeline, well or tank. Moreover, the data are processed in order to reconstruct an image of the spatial distribution of the relative electrical permittivity (also known as the dielectric constant) inside the tube, well or tank, which reflects the distribution of the different phases present in the flow.

21 Claims, 13 Drawing Sheets

U.S. PATENT DOCUMENTS

| | | | | |
|---|---|---|---|---|
| 7,280,710 | B1 * | 10/2007 | Castro-Pareja et al. | 382/303 |
| 2002/0114536 | A1 * | 8/2002 | Xiong et al. | 382/284 |

FOREIGN PATENT DOCUMENTS

| | | |
|---|---|---|
| EP | 1 251 459 | 10/2002 |
| GB | 2 214 640 | 9/1989 |
| GB | 2 329 476 | 3/1999 |

OTHER PUBLICATIONS

Gallagher K., Genetic algorithms: an evolution from Monte Carlo Methods for strongly non-linear geophysical optimization problems, Geophys. Res. Lett., 1991, vol. 18, pp. 2177-2180.

Goldberg D. E. Genetic Algorithms in Search, Optimization, and Machine Learning, 1989, Addison-Wesley, Reading, MA.

Gamio J. C., A High-sensitivity Flexible-excitation Electrical Capacitance Tomography System, PhD Thesis, 1997, University of Manchester Institute of Science and Technology, UK.

Gamio J. C., An interpretation of the linear back-projection algorithm used in electrical capacitance tomography, 2003, 3rd World Congress on Industrial Process Tomography, Banff, Canada.

Hammer E. A., Process tomography in the oil industry: state of the art and future possibilities, Measurement + Control, 1997, vol. 30, pp. 212-216.

Holland J. H., Adaptation in Natural and Artificial Systems, 1975, University of Michigan Press.

Maxwell J. C., A Treatise on Electricity and Magnetism, 1873, vol. I, Clarendon Press, pp. 88-97.

Metropolis N., Equation of state calculations by fast computing machines, J. Chem. Phys., 1953, vol. 21, No. 6, pp. 1087-1092.

Ortiz-Aleman C., Inversion of site response at Mexico City by using genetic algorithms and simulated annealing, EOS, Transactions of the American Geophysical Union, 1999, 80, 46, F708.

Ortiz-Aleman C., Three-dimensional modeling of aeromagnetic anomalies over the Chicxulub crater, Lunar and Planetary Science Conference, 2001, Proceedings CD vol. 32, Houston, Texas.

Ortiz-Aleman C., Inversion de la estructura del crater de chicxulub empleando metodos de inversion global, 2002, Revista Geofisica, 57, pp. 59-79.

Pilkington M., 3-D magnetic imaging using conjugate gradients, Geophysics, 1997, vol. 62, pp. 1132-1142.

Plaskowski A., Imaging Industrial Flows: Applications of Electrical Process Tomography, 1995, Institute of Physics Publishing, UK.

Rodríguez-Zúñiga J. L., Application of genetic algorithms to constrain shallow elastic parameters using in situ ground inclination measurements, Soil Dyn and Earth Eng. 1996, , vol. 16 (3), pp. 223-234.

Sambridge M., Genetic algorithms in seismic waveform inversion, Geophys J. Int., 1992, 109, pp. 323-342.

Sen M. K., Global Optimization Methods in Geophysical Inversion, 1995, Elsevier Science Publishers, Amsterdam, The Netherlands.

Stoffa P. L., Nonlinear multiparameter optimization using genetic algorithms: inversion of plane-wave seismograms, Geophysics, 1991, vol. 56, pp. 1794-1810.

Thorn R., Recent developments in three phase flow measurement, Measurement Science and Technology, 1997, vol. 8, pp. 691-701.

Vasudevan K., Simulated annealing static computation using an order-based energy function, Geophysics, 1991, vol. 56, pp. 1831-1839.

Vauhkonen M., A MATLAB package for the EIDORS project to reconstruct two-dimensional EIT images, Phys. Measurement, 2001, vol. 22, pp. 107-111.

Williams R. A., Process Tomography—Principles, Techniques and Applications, Butterworth Heinemann, 1995.

Xie C. G., 8-electrode capacitance system for two-component flow identification. Part 1: Tomographic flow imaging, IEE Proceedings A, 1989, vol. 136 (4), pp. 173-183.

Yamanaka H., Application of genetic algorithms to an inversion of surface-wave dispersion data, Bulletin of the Seismological Society of America, 1996, , vol. 36, pp. 436-444.

Yang W. Q., Image reconstruction algorithms for electrical capacitance tomography, Measurement Science and Technology, 2003, vol. 14(1), pp. R1-R13.

Yang et al., Image Reconstruction Algorithms for Electrical Capacitance Tomography, Meas. Sci. Technol. 14 (2003) pp. R1-R13.

Beck et al., Principles and Industrial Applications of Electrical Capacitance Tomography, Measurement + Control, vol. 30, Sep. 1997, pp. 197-200.

Xie et al., Electrical Capacitance Tomography for Flow Imaging: System Model for Development of Image Reconstruction Algorithms and Design of Primary Sensors, IEE Proc.-G, vol. 139, No. 1, Feb. 1992, pp. 89-98.

* cited by examiner

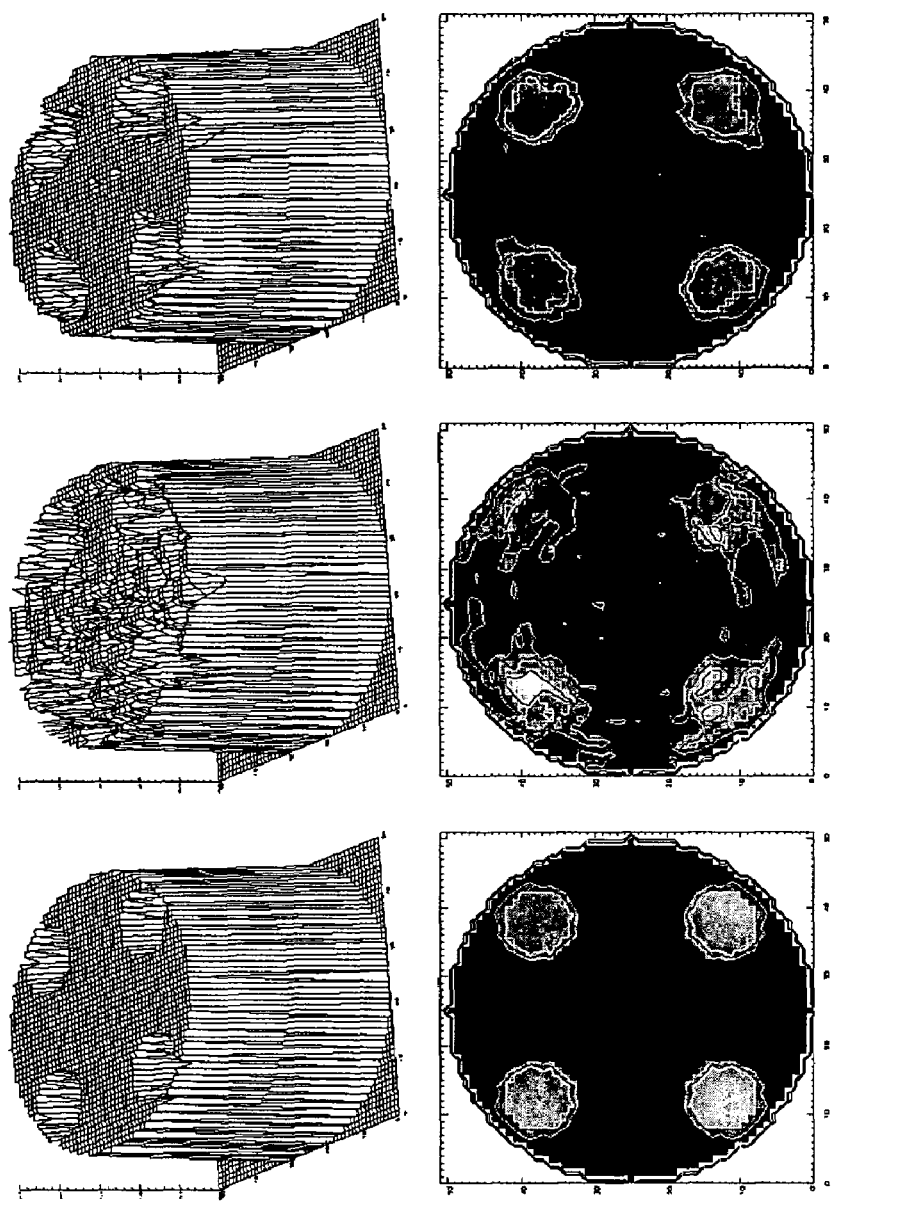

METHOD FOR IMAGING MULTIPHASE FLOW USING ELECTRICAL CAPACITANCE TOMOGRAPHY

PRIORITY

This application claims the benefit under 35 U.S.C. §119 (a)-(d) or §365(a)-(c), of an application filed under the Patent Coorporation Treaty ("PCT"), no. PCT/MX2003/000067 filed Aug. 22, 2003, the entire contents of which are hereby incorporated by reference.

TECHNICAL FIELD OF INVENTION

This invention relates to a new image reconstruction method for imaging multiphase flows using electrical capacitance tomography (ECT), it will be used in tomographic multiphase flow meters to quantify the various fluids (such as gas, oil and water) produced by an oil well. It can also be used to image and monitor other multiphase flows and processes occurring in industry, such as: optimization of design and operation of separator tanks, optimization of design of fluidized catalytic cracking units (FCC) and bed fluidized systems, and optimization of design of bed reactors.

BACKGROUND OF INVENTION

In general terms, tomography is used for obtaining an image of a cross section of an object in a given plane. X-ray tomography was the first to be developed (in 1970s) and its use is now routine not only in medicine but in some industrial applications as well (internal inspection of mechanical components and flaw detection in materials, for example).

Subsequently, a number of new tomographic methods aimed at industrial processes have emerged, collectively known as process tomography (Williams and Beck, 1995). The aim of these methods, which started to develop in the mid 1980s, is to produce an image of the phase or component distribution in an industrial process using only external sensors and without causing any perturbation to it, as depicted in FIG. 1, which shows a system of process tomography formed by a tank or pipe (A), a data acquisition system (B), and a computer for image reconstruction (C). In other words, process tomography provides a way of 'looking' from the outside to inside the process, with no need for physical intrusion or alteration, and this represents a radically different approach to gathering structural information on the process to a global scale, unlike the traditional methods based on local sampling on a certain number of points. The process may occur, for instance, in mixing or stirring vessels, fluidized bed reactors, separator tanks, or a pipeline carrying multiphase flow.

There is a whole range of principles and techniques that can be exploited in process tomography, including electrical methods based on impedance measurement, ultrasound, magnetic resonance, optical methods and those based on ionizing radiation (X- and gamma-rays). Generally speaking, ionizing radiation methods produce images with the highest definition, but are relatively slow. On the other hand, electrical methods yield low-resolution images but are much faster, robust and relatively inexpensive.

In particular with regard to electrical impedance tomography, or electrical tomography for short, there has been a very noticeable progress in the last few years. This type of tomography has two main modalities: capacitance tomography and resistance tomography. In a capacitance tomography system (Beck et al., 1997; Gamio, 1997; Plaskowski et al., 1995), (as depicted in FIG. 2, formed by a sensor (A), a data acquisition system (B) and an image reconstruction computer (C)), normally used with mixtures where the continuous phase is non-conducting, the sensor employed, as depicted in FIGS. 3 and 4, is made of a circular array of electrodes (B) distributed around the cross-section to be examined, and the capacitance between all the different electrode-pair combinations is measured. With the help of a computer and a suitable image reconstruction algorithm, this information is used to create a map (an image) showing the variation of the dielectric constant (or relative permittivity) inside the sensor area, thus providing an indication of the physical distribution of the various components of the mixture. Relative to FIGS. 3 and 4, the electrodes (B) can be located on the outside of a non-conducting pipe (A), in order to simplify sensor construction and avoid direct contact with the process fluids (E). A second external grounded metallic pipe (C) serves as an electric screen and to provide mechanical resistance. The sensor also has two cylindric guard electrodes (D) that are grounded as well.

The British patent GB 2 214 640, issued Sep. 6, 1989, describes an electrical capacitance tomography system that employs a linear back-projection (LBP) algorithm as the image reconstruction method. However, such reconstruction method produces images of a relatively low definition.

Resistance tomography, on the other hand, is aimed at mixtures where the continuous phase is a conductor of electricity (Plaskowski et al., 1995; Williams y Beck, 1995). In this case, the electrodes are installed flush with the inside surface of the pipe (or vessel) wall and in direct contact with the fluids. A number of different excitation current patterns are applied and the resultant voltages are measured. They are then used to construct a map of the conductivity distribution inside the sensor, which reflects the physical distribution of the mixture components.

In principle, electrical capacitance tomography (ECT) has important applications in multiphase flow measurement, particularly gas-oil two-phase flow, which often occurs in many oil wells. The traditional way to quantify the various fluids produced by an oil well is to separate the mixture by gravity in large tanks, prior to measuring each component separately using conventional single-phase flow meters. In the last decades, multiphase flow meters have appeared which allow the quantification of the produced fluids without the need to separate the mixture (Thorn et al., 1997). However, the multiphase meters currently available suffer from an unwanted sensibility to changes in the flow regime, unless they are equipped with flow mixing or conditioning devices that introduce permanent pressure losses (which ultimately translate into energy loss). This limitation should be avoided through ECT as the flow regime could be determined and used to compensate the response of conventional multiphase meters, or, alternatively, it is possible to design a new type of tomographic multiphase meter, based on analyzing series of ECT images from two slightly separated cross-sections of the pipe (Hammer et al., 1997; Plaskowski et al., 1995). Additionally, ECT has potential applications to imaging, monitoring and controlling numerous industrial multiphase processes.

However, so far the main limiting factor to the practical application of ECT has been the lack of fidelity or accuracy of the images obtained using the available image reconstruction methods, giving rise to a need of improved methods as the one introduced in this invention (Yang y Peng, 2003). Simple direct methods like linear back-projection (LBP) yield relatively poor images that only provide a qualitative indication of the component distribution inside the sensor. One said method is described in British patent GB 2214640, issued Sep. 6, 1989.

On the other hand, more sophisticated methods, based on iterative local optimization techniques, generally require one or more regularization parameters whose optimal value depends precisely on the (unknown) image to be reconstructed, apart from the fact that the regularization employed has the effect of smoothing the image contours, making it more diffuse. One said method is described in British patent GB 2329476 A (issued Mar. 24, 1999).

Thus, there is an urgent need of better and more accurate image reconstruction methods. As an example of this, a patent was issued recently covering an image reconstruction method based on the application of artificial neural networks (American patent U.S. Pat. No. 6,577,700 B1, issued Jul. 10, 2003).

The present invention describes new image reconstruction methods based on simulated annealing and genetic algorithms. According to the laws of physics, electrostatics in particular, the ECT sensor (as can be observed in FIG. 4) can be considered as a special case of a system of charged conductors separated by a dielectric medium, the theory of which was first developed by J. C. Maxwell (1873). In our particular case, the sensor electrodes (B) act as the charged conductors while the insulating pipe end (A) the sensor contents acts as the dielectric medium. For an n electrode sensor, the induced electrode charges $q_i$ and the electrode potentials $v_i$ are related by the following set of linear equations $$q_1 = c_{11}v_1 + c_{12}v_2 + \ldots + c_{1n}v_n \quad (1)$$
$$q_2 = c_{21}v_1 + c_{22}v_2 + \ldots + c_{2n}v_n$$
$$\vdots \quad \vdots \quad \vdots \quad \vdots$$
$$q_n = c_{n1}v_1 + c_{n2}v_2 + \ldots + c_{nn}v_n$$

where $c_{ii}$ are the self-capacitance coefficients (or just self-capacitances for short) of electrode i, while the others, $c_{ij}$, with $i \neq j$, are the mutual capacitance coefficients (or just mutual capacitances) between electrodes i and j. Put in matrix form, equation (1) becomes $$\begin{bmatrix} q_1 \\ q_2 \\ \vdots \\ q_n \end{bmatrix} = \begin{bmatrix} c_{11} & c_{12} & \ldots & c_{1n} \\ c_{21} & c_{22} & \ldots & c_{2n} \\ \vdots & \vdots & \ddots & \vdots \\ c_{n1} & c_{n2} & \ldots & c_{nn} \end{bmatrix} \begin{bmatrix} v_1 \\ v_2 \\ \vdots \\ v_n \end{bmatrix} \quad (2)$$

or $$q = Cv \quad (3)$$

Since the capacitances have the property of reciprocity, i.e., $c_{ij} = c_{ji}$, there are only $m = \frac{1}{2}n(n-1)$ independent mutual capacitances, corresponding to lower (or upper) triangular matrix of C, and corresponding also to each one of the m different electrode-pairs that can be formed in the sensor.

The value of the mutual capacitances is a complex non-linear function of the conductor system geometry, and of the spatial distribution of the dielectric constant or relative permittivity (hereafter called just 'permittivity') of the dielectric medium. In the case of the ECT sensor, the geometry of the electrodes, that of the pipe, and the value of the dielectric constant of the latter, are all fixed. Therefore, it can be said that the mutual capacitances are a function only of the spatial distribution of the dielectric constant inside the sensor, $\in(x,y)$. The problem of calculating the mutual capacitances corresponding to a specific permittivity distribution inside the sensor is referred to as the forward problem.

The use of the cylindrical end guards (FIG. 3) and the assumption that the phase (and thus the permittivity) distribution does not change too much in the axial direction, allows the sensor to be represented by a two-dimensional (2-D) model (Xie et al., 1989). Unless otherwise stated explicitly, in what follows a 2-D model of the sensor will be used. Therefore, the electric charges $q_i$ and the capacitances $c_{ii}$ y $c_{ij}$ that appear in equations (1) and (2) should be considered quantities per unit length of the electrodes in the axial direction. A tilde (i.e., $\tilde{q}_i$, $\tilde{c}_{ii}$ and $\tilde{c}^{ij}$) shall be used to denote the total quantities that result from considering the actual length of the electrodes. The previous variables are related between them through the electrode length L, according to $$q_i = \frac{\tilde{q}_i}{L}, \; c_{ii} = \frac{\tilde{c}_{ii}}{L} \text{ and } c_{ij} = \frac{\tilde{c}_{ij}}{L} \quad (4)$$

If the interior of the 2-D sensor is divided into p equal-area regions (or 'pixels') where the permittivity is considered constant, then the discrete version of the forward problem is $$c = \begin{bmatrix} c_1 \\ \vdots \\ c_m \end{bmatrix} = f(\varepsilon) = \begin{bmatrix} f_1(\varepsilon) \\ \vdots \\ f_m(\varepsilon) \end{bmatrix} \text{ with } \varepsilon = \begin{bmatrix} \varepsilon_1 \\ \vdots \\ \varepsilon_p \end{bmatrix} \quad (5)$$

where c is the vector of mutual capacitances (per unit length), $f_i$ are non-linear functions not known explicitly and $\in$ is the vector of permittivities corresponding to the p regions or pixels within the sensing zone.

Applying Gauss's Law, the mutual capacitances per unit axial electrode length can be calculated as $$c_{ij} = \frac{q_i}{v_j} = -\frac{\varepsilon_0}{V} \oint_{\Gamma_i} (\varepsilon \nabla \phi^j) \cdot dl = -\frac{\varepsilon_0}{V} \oint_{\Gamma_i} \varepsilon \frac{\partial \phi^j}{\partial n} dl \quad (6)$$

where $\in_o$ is a physical constant called the permittivity of free space, equal to $8.854 \times 10^{-12}$ farads per meter, $\in_i$ is a closed curve surrounding electrode i, dl is a normal vector representing an element of the curve $\Gamma_i$, dl is an element of length of that curve, the symbol '•' represents the scalar product of two vectors, and $\phi^j$ is the electrostatic potential produced in the sensor when applying a voltage of V volts to electrode j (which is called source or excitation electrode) and 0 volts to all others (called detection electrodes).

The potential $\phi^j$ is determined by the solution of the following partial differential equation $$\nabla \cdot \in(x,y) \nabla \phi^j = 0 \quad (7)$$

subject to the boundary conditions (a) $\phi^j = V$ volts on the source electrode and (b) $\phi^j = 0$ on the detection electrodes and the outer screen. In general, equation (7) does not have an analytic solution and must be solved numerically.

The problem of estimating what is the spatial permittivity distribution inside the sensor that corresponds to a specific set of mutual capacitance values is referred to as the inverse problem, and is the problem that image reconstruction methods must address and solve. Normally, the permittivity estimation is made in a discrete way, representing it as a vector $\in$ like the one in equation (5), which must be calculated from a vector of observed mutual capacitances c, obtained using of a suitable measurement apparatus.

In order to solve the inverse problem, most ECT systems employ the linear back-projection algorithm (LBP) (Plaskowski et al., 1995; Yang y Peng, 2003; Xie et al., 1989, 1992), which is described next. As a first step, a sensitivity map must be calculated for each one of the $m=\frac{1}{2}n(n-1)$ possible electrode pairs, given by $$s_i(k) = \frac{c_i(k) - c_{i(emp)}}{c_{i(full)} - c_{i(emp)}} \text{ for } i = 1, \ldots, n \quad (8)$$

where k is the pixel number (from 1 to p), $c_i(k)$ is the capacitance measured with electrode pair i when the area of pixel k is full of a high-permittivity material while the rest of the sensor is full of a low-permittivity material, whereas $c_{i(full)}$ and $c_{i(emp)}$ are the capacitances for electrode pair i when the sensor is full of high- and low-permittivity material, respectively. Generally, these sensitivity maps are calculated by solving numerically equation (7) and applying equation (6).

Having determined the sensitivity maps, they can be used to obtain a permittivity image from any vector of $m=\frac{1}{2}n(n-1)$ measured mutual capacitances, c, corresponding to some unknown material distributions inside the sensor. For this, the measured capacitance readings must first be normalized according to $$\lambda_i(k) = \frac{c_i - c_{i(emp)}}{c_{i(full)} - c_{i(emp)}} \quad (9)$$

where $\mu_i$ is the normalized capacitance for electrode pair i and $c_i$ is the actual capacitance measured with that electrode pair.

The basic LBP formula calculates a 'grey level' g(k) for each pixel as $$g(k) = \frac{\sum_{i=1}^{m} \lambda_i s_i(k)}{\sum_{i=1}^{m} s_i(k)} \text{ for } k = 1, \ldots, p \quad (10)$$

In principle, this grey level is supposed to be linearly related to the permittivity, with g=1 and g=0 corresponding to the permittivities of the high- and low-permittivity materials, respectively. LBP is based on making a linear approximation to a problem that, as already mentioned, is essentially non-linear (Gamio and Ortiz-Aleman, 2003). Therefore, this image reconstruction method causes considerable errors, which are particularly grave if there are large differences in permittivity in the image.

So far, the main alternative to LBP has been the use of iterative methods that seek to minimize some objective function, employing local optimization techniques like the regularized Newton-Raphson method or other similar approaches (Yang and Peng, 2003). As an example of these methods, there is the one used in the EIT2D software package (Vauhkonen et al., 2001), developed by researchers from Finland and the United Kingdom. Their method is based on minimizing, with respect to $\in$, the following functional $$\|c_{meas} - c_{calc}\|^2 + \alpha^2 \|L\in\|^2 \quad (11)$$

where $\alpha$ is a regularization parameter, L is a 'regularization' matrix containing some type of a-priori smoothness information about c, and $c_{calc}=f(\in)$ is the vector of n calculated mutual capacitance values for a given permittivity distribution inside the sensor. Starting with an initial guess $\in_o$, the minimization is carried out by the following iterative procedure (basically a Newton-type method with Tikhonov regularization)

$$\in_{k+1} = \in_k + [J_k^T J_k + \alpha^2 L^T L]^{-1} \{J_k^T [c_{meas} - f(\in_k)] - \alpha^2 L^T L \in_k\} \quad (12)$$

where $J_k$ is the so-called Jacobian matrix of the partial derivatives of $f(\in)$, evaluated at $\in_k$ $$J_k = J(\varepsilon_k) = \left[\frac{\partial f_i}{\partial \varepsilon_j}\bigg|_{\varepsilon_{k_j}}\right] (i = 1 \ldots m, j = 1 \ldots p) \quad (13)$$

However, these image reconstruction methods have the problem that they require, for their correct operation, one or more regularization parameters whose right value is strongly dependent, precisely, on the image that one wishes to reconstruct, implying that one would need to know beforehand the solution to the problem. Moreover, these methods produce distorted images, because the regularization has an excessive smoothing effect on the obtained permittivity. If the regularization is too strong the smoothing effect will occur, and if it is too weak the method can become unstable and/or not converge to the desired solution.

These local optimization algorithms, during their search, explore only a relatively small sector of the solution domain, restricted to the vicinity of the initial guess. If the optimal solution of the problem, i.e., the absolute minimum of the objective function, is located far from the initial guess, it will hardly be reached due to the presence of relative minima in their way, places where these methods can become trapped. The most used methods in this category are least-squares linear inversion and techniques that utilize the gradient of the objective function, like the steepest-descent and the conjugate-gradient methods. In general, local search methods exploit the (scarce) information derived from the comparison of a small number of models (solutions), thus avoiding an extensive search in the whole model space (Sambridge y Drijkoningen, 1992).

Global optimization methods explore the whole solution domain during the inversion process. They carry out an extensive scan within the model space. In this way, despite the existence of partial solutions to the problem, there is a greater possibility that the final solution corresponds to the best fit between the observed data and the synthetic ones. This type of methods, contrary to local techniques, does not require the information provided by the derivatives of the objective function, because in this case the problem does not need to be linearized. Global optimization algorithms use stochastic criteria in order to simultaneously explore all the solution space in search of the optimal model. The best known of the global methods is Monte Carlo, which performs a purely random and unbiased search. In other words, when generating each new model, it does not take advantage of the information obtained from the previously evaluated models (Gallagher et al., 1991). The unguided randomness is the most characteristic feature of this method, which distinguishes it from the rest of the global methods. Among the global optimization techniques, there are also the method of simulated annealing and genetic algorithms. Both were conceived as analogies of optimization systems occurring in nature. Genetic algorithms emulate the mechanisms of biological evolution while simulated annealing is based on thermodynamics. Both methods are inherently non-linear and, therefore, lend themselves naturally to their application in capacitance tomography, a non-linear problem.

SPECIFICATION

The present invention refers to an image reconstruction method for imaging multiphase flows using electrical capacitance tomography (ECT), based on the use of heuristic non-linear techniques of global optimization, particularly the simulated annealing method and genetic algorithms. It considers a circular array of rectangular contiguous metallic electrodes placed around the outer wall of a pipe made of an electrically insulating material, forming a sensor. Trough the sensor flows a mixture of fluids in the form of a multiphase flow, whose spatial distribution inside the sensor is to be determined. Data are obtained by performing mutual capacitance measurements between all possible electrode pairs. Said data depend on the fluid distribution inside the pipe.

A matter of this invention is to provide a method to process said data in order to reconstruct an image of the spatial distribution of the phases or components of the multiphase mixture that flows through the sensor, using the method of simulated annealing and/or genetic algorithms.

Another matter of this invention is that it can be used in tomographic multiphase flow meters to quantify the various fluids (such as gas, oil and water) produced by an oil well.

Another matter of the present invention is that it can also be used to image and monitor other multiphase flows and processes occurring in industry, such as optimization of design and operation of separator tanks, optimization of design of fluidized catalytic cracking units (FCC) and bed fluidized systems, and optimization of design of bed reactors.

REFERENCES

Beck M. S., Byars M., Dyakowski T., Waterfall R., He R., Wang S. M. and Yang W. Q. 1997, Principles and industrial applications of electrical capacitance tomography, *Measurement+Control*, Vol. 30, pp. 197-200.

Cruz-Atienza V. M. 1999, *Inversion global con algorithmos geneticos y cristalizacion simulada aplicada a funciones de receptor: modelos estructurales de velocidades para la corteza en la Republica Mexicana*. Tesis, Facultad de Ingenieria, UNAM.

Gallagher K., Sambridge M. and Drijkoningen G. 1991, Genetic algorithms: an evolution from Monte Carlo Methods for strongly non-linear geophysical optimization problems, *Geophys. Res. Lett.*, 18, pp. 2177-2180.

Goldberg D. E. 1989, *Genetic Algorithms in: Search, Optimization, and Machine Learning*, Addison-Wesley, Reading, Mass.

Gamio J. C. 1997, *A High-sensitivity Flexible-excitation Electrical Capacitance Tomography System*, PhD Thesis, University of Manchester Institute of Science and Technology, UK.

Gamio J. C. and Ortiz-Aleman J. C. 2003, An interpretation of the linear back-projection algorithm used in electrical capacitance tomography, *3rd World Congress on Industrial Process Tomography*, Banff, Canada (in press).

Hammer E. A. and Johansen G. A. 1997, Process tomography in the oil industry: state of the art and future possibilities, *Measurement+Control*, Vol. 30, pp. 212-216.

Holland J. H. 1975, *Adaptation in Natural and Artificial Systems*, University of Michigan Press.

Maxwell J. C. 1873, *A Treatise on Electricity and Magnetism (Vol. I)*, Clarendon Press, pp. 88-97.

Metropolis N., Rosenblueth A., Rosenblueth M., Teller A. and Teller E. 1953, Equation of state calculations by fast computing machines, *J. Chem. Phys.*, 21, pp. 1087-1092.

Ortiz-Aleman C., Iglesias-Mendoza A., Cruz-Atienza V. M. 1999, Inversion of site response at Mexico City by using genetic algorithms and simulated annealing, *EOS, Transactions of the American Geophysical Union*, 80, 46, F708.

Ortiz-Aleman C., Urrutia-Fucugauchi J. and Pilkington M. 2001, Three-dimensional modeling of aeromagnetic anomalies over the Chicxulub crater, *Lunar and Planetary Science Conference*, Proceedings CD Volume, 32, Houston, Tex.

Ortiz-Aleman C., Urrutia-Fucugauchi J. and Iglesias-Mendoza A. 2002, Inversion de la estructura del crater de chicxulub empleando metodos de inversion global, *Revista Geofisica*, 57, pp. 59-79.

Ortiz-Aleman C. and Urrutia-Fucugauchi J., 2003, Central zone structure and magnetic sources in the Chicxulub crater as derived from three-dimensional modeling of aeromagnetic anomalies, *Earth, Planets and Space* (in press).

Pilkington M. 1997, 3-D magnetic imaging using conjugate gradients, *Geophysics*, 62, pp. 1132-1142.

Plaskowski A., Beck M. S., Thorn R. and Dyakowski T. 1995, Imaging Industrial Flows Applications of Electrical Process Tomography, Institute of Physics Publishing, UK.

Rodriguez-Zúñiga J. L., Ortiz-Aleman C., Padilla G. and Gaulon R. 1996, Application of genetic algorithms to constrain shallow elastic parameters using in situ ground inclination measurements, *Soil Dyn and Earth Eng*, 16 (3), pp. 223-234.

Sambridge M. and Drijkoningen G. 1992, Genetic algorithms in seismic waveform inversion, *Geophys J. Int.*, 109, pp. 323-342.

Sen M. K. and Stoffa P. L. 1995, *Global Optimization Methods in Geophysical Inversion*, Elsevier Science Publishers, Amsterdam, The Netherlands.

Stoffa P. L. and Sen M. K. 1991, Nonlinear multiparameter optimization using genetic algorithms: inversion of plane-wave seismograms, *Geophysics*, 56, pp. 1794-1810.

Thorn R., Johansen G. A. and Hammer E. A. 1997, Recent developments in three phase flow measurement, *Measurement Science and Technology*, Vol. 8, pp. 691-701.

Vasudevan K., Wilson W. G. and Ladilaw W. 1991, Simulated annealing static computation using an order-based energy function, *Geophysics*, vol. 56, pp. 1831-1839.

Vauhkonen M., Lionheart W. R. B., Heikkinen L. M., Vauhkonen P. J. and Kaipio J. P. 2001, A MATLAB package for the EIDORS project to reconstruct two-dimensional EIT images, *Phys. Measurement*, 22, pp. 107-111.

Williams R. A. and Beck M. S. (eds) 1995, *Process Tomography—Principles, Techniques and Applications*, Butterworth Heinemann.

Xie C. G., Plaskowski A. and Beck M. S. 1989, 8-electrode capacitance system for two-component flow identification. Part 1: Tomographic flow imaging, *IEE Proceedings A*, 136 (4), pp. 173-183.

Xie C. G., Huang S. M., Hoyle B. S., Thorn R., Lenn C., Snowden D. and Beck M. S. 1992, Electrical capacitance tomography for flow imaging: System model for development of image reconstruction algorithms and design of primary sensors, *IEE Proc.-G*, 139 (1), pp. 89-98.

Yamanaka H. and Ishida H. 1996, Application of genetic algorithms to an inversion of surface-wave dispersion data, *Bulletin of the Seismological Society of America*, 36, pp. 436-444.

Yang W. Q. and Peng L. 2003, Image reconstruction algorithms for electrical capacitance tomography, *Measurement Science and Technology*, 14(1), pp. R1-R13.

BRIEF DESCRIPTION OF THE DRAWINGS

FIG. 13 shows the results obtained by reconstructing images of a simulated gas-oil bubbly flow, using the simulated annealing method in the present invention.

DETAILED DESCRIPTION

The new image reconstruction procedures of the present invention are based on heuristic global optimization methods, specifically simulated annealing and genetic algorithms.

Figure 1:
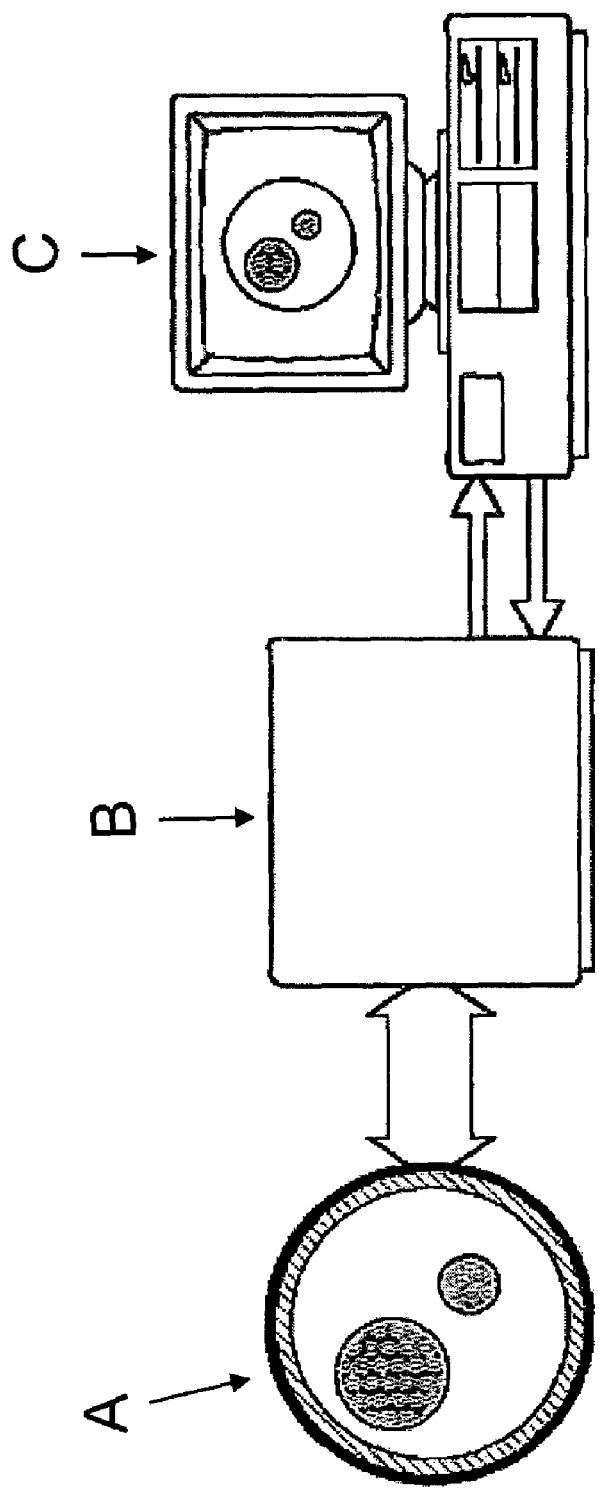
FIG. 1 represents schematically a process tomography system employed in the present invention.
Figure 2:
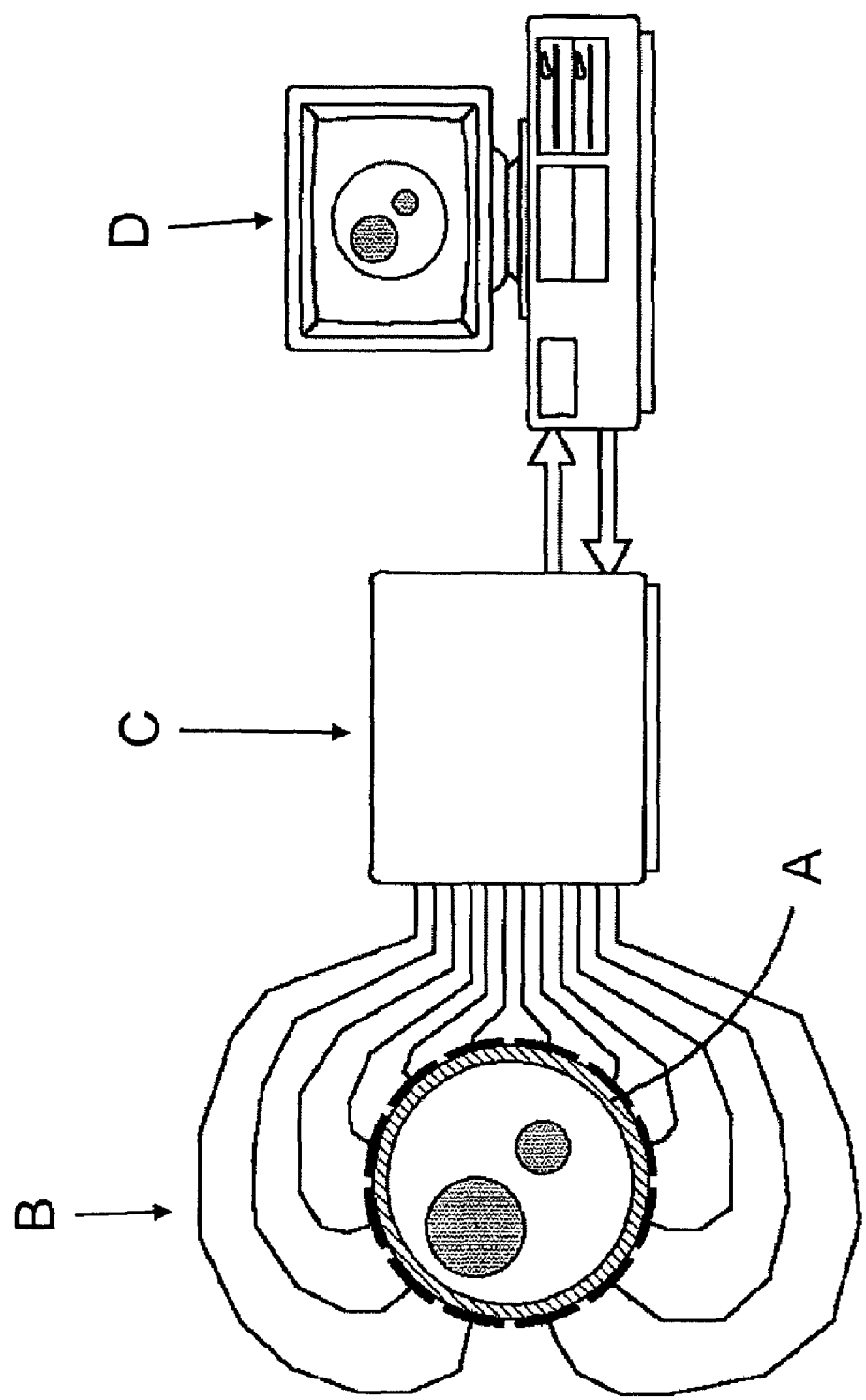
FIG. 2 represents schematically an electrical capacitance tomography system employed in the present invention.
Figure 3:
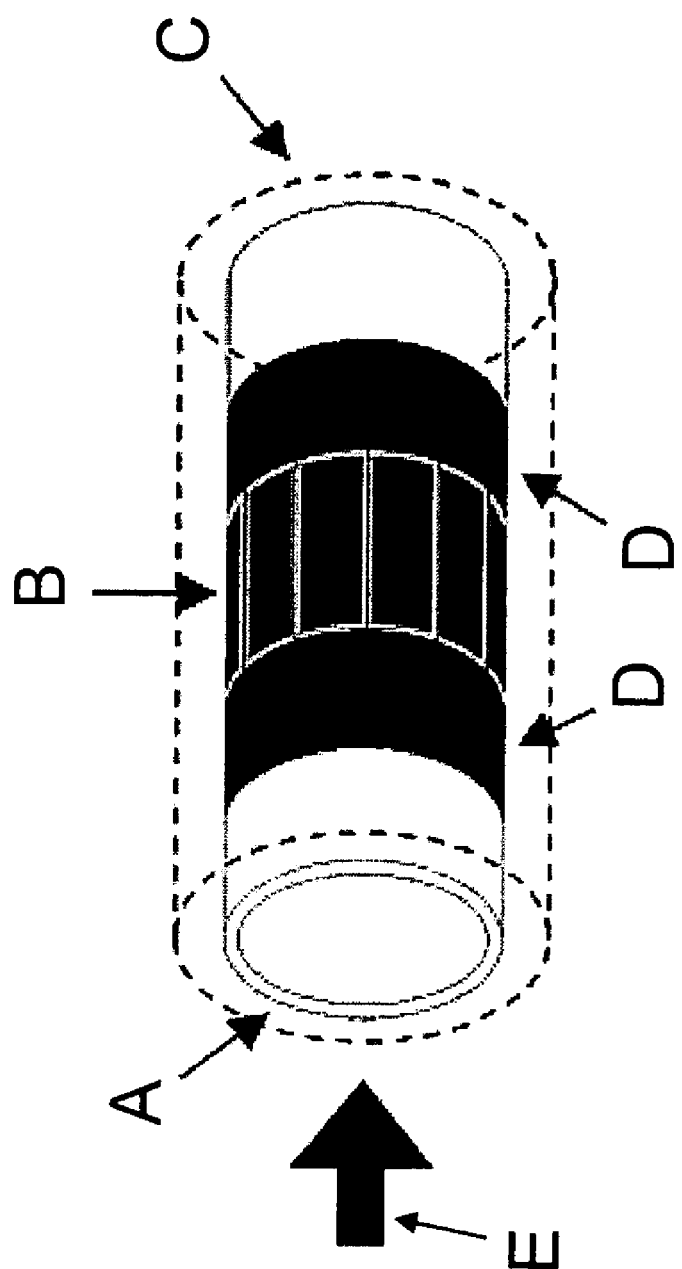
FIG. 3 shows a drawing of the sensor employed in capacitance tomography used in the present invention.
Figure 4:
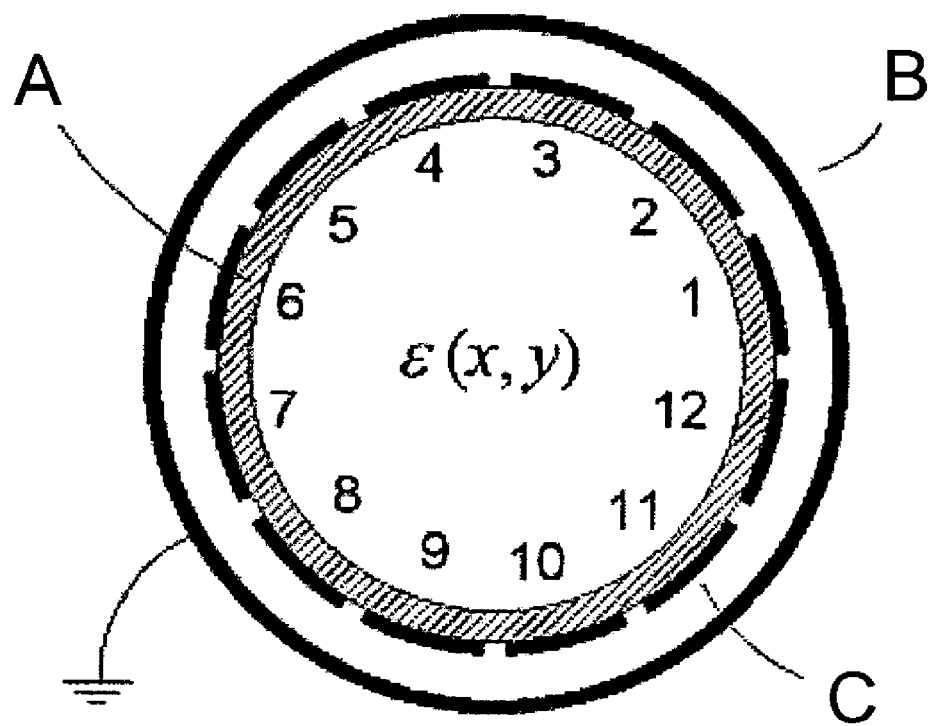
FIG. 4 shows a cross-section of the sensor at the zone of the measuring electrodes employed in the present invention.

A plurality of n metallic electrodes is placed around the periphery of a region to be imaged and electrical measurements of capacitance or resistance are collected between them. That is to say, m=½n(n−1) measurements (or data) are obtained. It is preferred that the data is capacitance data but it can also be resistance data. As shown in FIG. 3, the electrodes (B) can be rectangular in shape and be placed on the outer wall of a pipe (A) made of electrically non-conducting material, thus forming a sensor, which contains a multiphase or multicomponent flow (E). The aim is to use said measurement data to reconstruct an image of the spatial distribution of the dielectric constant (or permittivity) within the imaged region. Said permittivity distribution reflects the distribution of the substances filling the interior of the sensor, where the imaging area is. This area shall be considered divided into p equal parts.

Method of Simulated Annealing

The simulated annealing method is based on an analogy with the thermodynamic process of crystallization. A mineral fluid that cools slowly until it reaches a low energy state, gives rise to the formation of well defined crystals. If, on the contrary, the substance leaves its thermal equilibrium state with a sudden or partial cooling, the resulting crystal will have many defects, or the substance may even form a 'glass', characterized by its meta-stable molecular disorder. This concept is used in the context of optimization methods to recognize potentially useful models or configurations.

The atoms of each molecular configuration are equivalent to the model parameter in the inverse problem (i.e., the permittivity of the various image pixels). The system energy for such configuration is related to the cost (or misfit) function associated with the set of parameters involved in the model. In our case, the system energy is associated with the following $L_2$ norm $$E = L_2 = \frac{\sum_{i=1}^{m}[c(i)_{meas} - c(i)_{calc}]^2}{\sum_{i=1}^{m}[c(i)_{meas}]^2} \quad (i=1,\ldots,m) \tag{14}$$

where $c(i)_{meas}$ are the m measured capacitances and $C(i)_{calc}$ are the ones calculated by solving the forward problem for a given permittivity distribution ∈. From an initial permittivity distribution, the method generates a range of configurations or parameter combinations considering a certain temperature T for the process. For this purpose the Metropolis et al. (1953) criterion is employed, which consists in changing a parameter, in each iteration, by a small random amount. This shift causes a change ΔE in the system's total energy. If ΔE is less than or equal to zero, the change in the parameter is accepted and the resulting configuration is considered as the new current configuration. When there is an increase in the system energy (ΔE is greater than zero), the probability of acceptance or rejection for the parameter change is determined as $$P(\Delta E) = e^{-\Delta E/T} \tag{15}$$

In order to decide whether or not a change that produces an increase in the system energy is accepted, a random number between cero and one is chosen, which is then compared with the value of the probability corresponding to ΔE. If said random number is smaller, the parameter shift is accepted and the new configuration is considered as the current (updated) one. If said random number is greater, the parameter shift is not accepted and the configuration that existed before the shift is maintained. Repeating this procedure continuously, the thermal movement of the atoms of a system in thermal equilibrium (at a fixed temperature T) is simulated. I order to reach the system's base state, that is to say, the state of lowest energy and highest order, the temperature must be reduced very slowly, simulating a quasi-static process. This means that, during the cooling, the system must experience a series of states infinitesimally separated from the state of thermal equilibrium.

Figure 5:
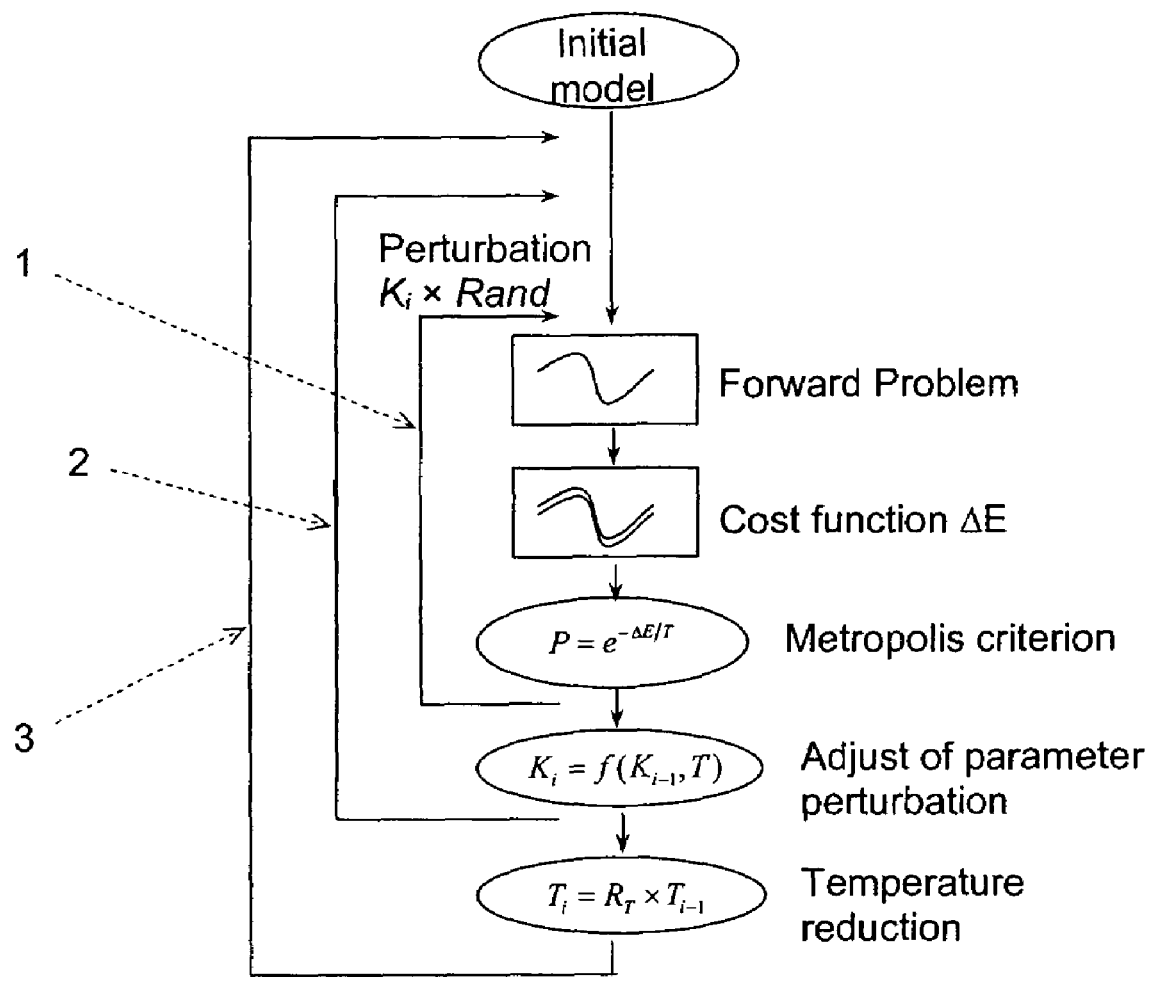
FIG. 5 is a schematic drawing illustrating the method of simulated annealing employed in the present invention.

The method of simulated annealing has three basic components (Vasudevan, 1991): an energy (or cost, or misfit) function, an order function (the Metropolis criterion), and a parameter that controls the system temperature. The process consists of three nested cycles. FIG. 5 shows a diagram that illustrates the method of the present invention. The external cycle (3) regulates the system temperature. Every time a cycle is completed, the temperature decreases as it is multiplied by a factor $R_T$ that is normally very close to one ($0R_T<1$). In this way the desired slow and gradual cooling is carried out. The intermediate cycle (2) updates the values, independent of each other, of a series of constants $K_i$ associated with each parameter. Said constants determine the maximum change that each parameter may experience when it is perturbed in the innermost cycle (1). The value of said constants depends on the number of times that the current model has been accepted (according to the Metropolis criterion) at the end of every sequence of internal cycles (1). In the internal cycle (1) the parameter values are perturbed using the factors $K_i$, defined in the intermediate cycle (2). The perturbation is done multiplying each parameter by the product of its corresponding $K_i$ times a randomly chosen number between minus one and one. After this, the synthetic response of the current model is calculated and the change in the system's energy associated with the new parameter configuration is evaluated. Said energy change corresponds to the misfit between the synthetic data curve and the observed or measured one. If the misfit decreases, then the new configuration will be accepted as the current one and in turn perturbed in the same way. If, on the contrary, if the random perturbation causes an increase in the misfit, associated with an increment in the energy E, then that configuration is assigned a probability of acceptance according to the Metropolis criterion.

The cycles (1), (2) and (3) of FIG. 5 are repeated, while the temperature of the process decreases progressively. As the temperature diminishes, the parameter variations are smaller and smaller. In this way, the search in the solutions domain tends to confine itself towards the models associated with the absolute minimum of the misfit function E. The end result is a set of values for the parameters (i.e., the permittivity in the various pixels that make an image) whose synthetic response reproduces the observed (capacitance) data, with a sufficiently small error.

Figure 6:
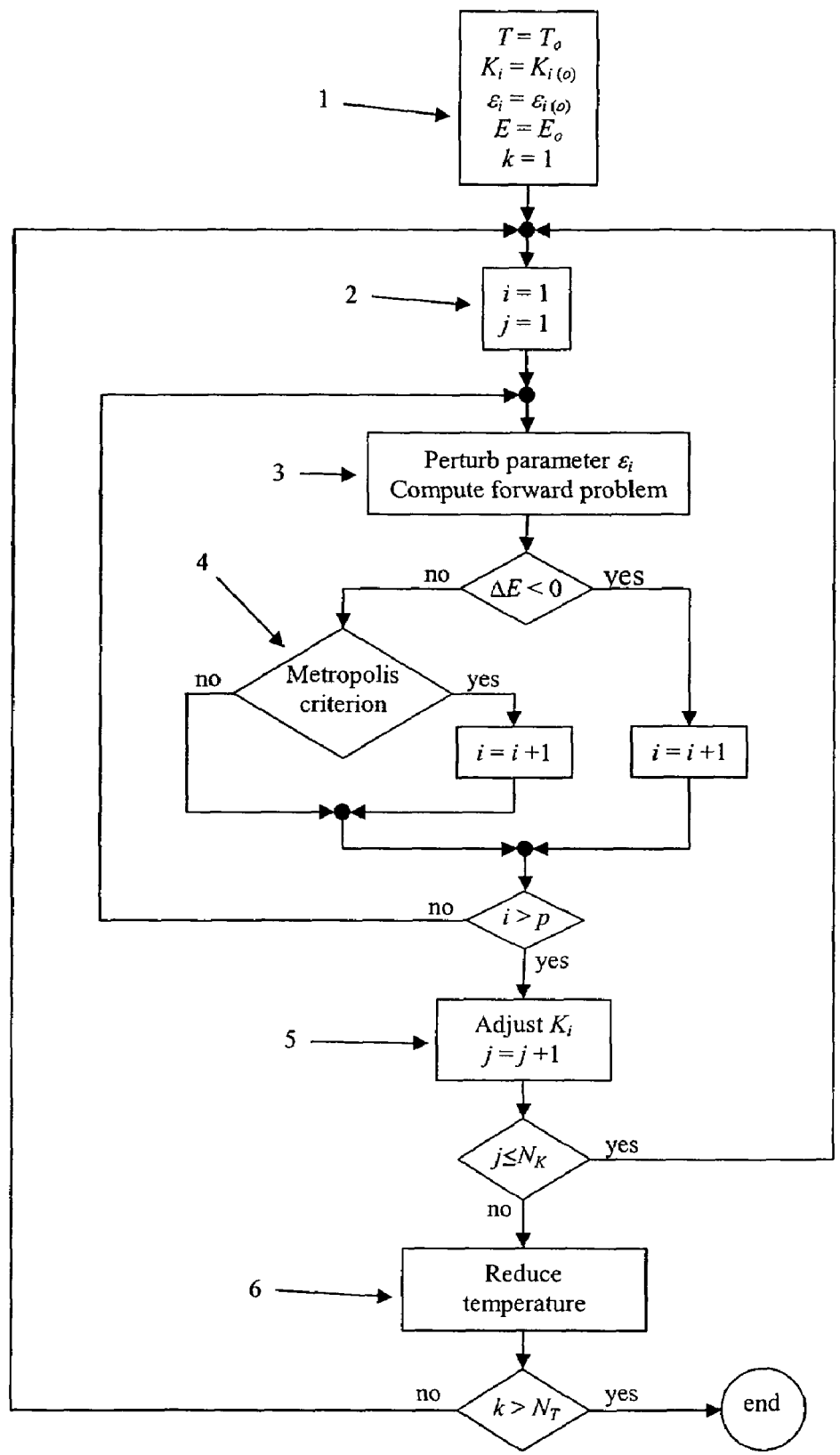
FIG. 6 shows the flow diagram of one possible implementation of the method of simulated annealing employed in the present invention.

As an example, one possible specific embodiment of, albeit not the only one, of the method of simulated annealing, is presented in FIG. 6. The method starts in block (1), with a series of initial values for the temperature, the perturbation constants, the permittivities and the cost or misfit function $(T_o, K_{i(o)}$ y $\in_{i(o)}$ (con i=1, ..., p) y $E_o$), and initializing the external cycle counter, denoted by k. Next, in block (2) the counters for the internal and intermediate cycles, i and j, are initialized, and the internal cycle starts. In it, one by one the parameters (or permittivities) are subject to a random perturbation in block (3). Still in block (3), each time a parameter is perturbed, the forward problem is solved and the cost or misfit function, E, is calculated applying equation (14). If there was a decrease of E with respect to the previous evaluation of it, the perturbed parameter value is accepted as the new current value, the internal cycle parameter counter i is increased by one, and the method proceeds to perturb the next parameter (if there is one). If, on the contrary, there was an increase in E, then the Metropolis criterion is applied, in block (4), in order to decide whether or not the perturbed parameter value is accepted as the new current one. If, according to said criterion, the new value is accepted, then the internal cycle counter i is incremented by one and the method proceeds to perturb the next parameter (if there is one). If, according to the metropolis criterion, the perturbed value is not accepted, then the counter i is not incremented and the method proceeds to perturb once again the same parameter. Once all parameters $\in_i$ have been updated, in block (5) the value of the constants $K_i$ (which determine how the parameters are perturbed within the internal cycle) is adjusted, and the intermediate cycle counter j is increased by one. $N_K$ determines how many times the internal cycle will be repeated without reducing the temperature. In other words, the intermediate cycle consists in the repetition of the internal cycle $N_K$ times, but with different values for $K_i$. This is done so in order to prevent the temperature from descending too fast, which can have negative effects in some simulated annealing applications. However, in the present invention that does not happen, and the value of $N_K$ is taken as one. At the end of the intermediate cycle, in block (6) the temperature is reduced as indicated in previous paragraphs and the external cycle counter k is increased by one. The whole previous procedure is repeated until k reaches the iteration limit $N_T$, or before that if a sufficiently low value for the cost function E is obtained.

The present invention also refers to a image reconstruction method based on genetic algorithms, that is described in the next section.

Method of Genetic Algorithms

Genetic algorithms, originally proposed by Holland (1975), represent an evolution of the Monte Carlo method for strongly non-linear problems. The search for the optimum model is carried out exploring simultaneously the whole solution space, employing a probabilistic transition rule to guide the search. The process starts from a set of randomly chosen models.

The parameters of each model are transformed into binary code in order to form chains called chromosomes, which are then subject to natural and genetic selection criteria. The processes of selection, crossover and mutation update the population of models, originating a new generation of chromosomes, emulating the way in which biological evolve to produce organisms better adapted to the environment. The whole process is repeated until the measure of the misfit function approaches the maximum fit for all the population.

Figure 7:
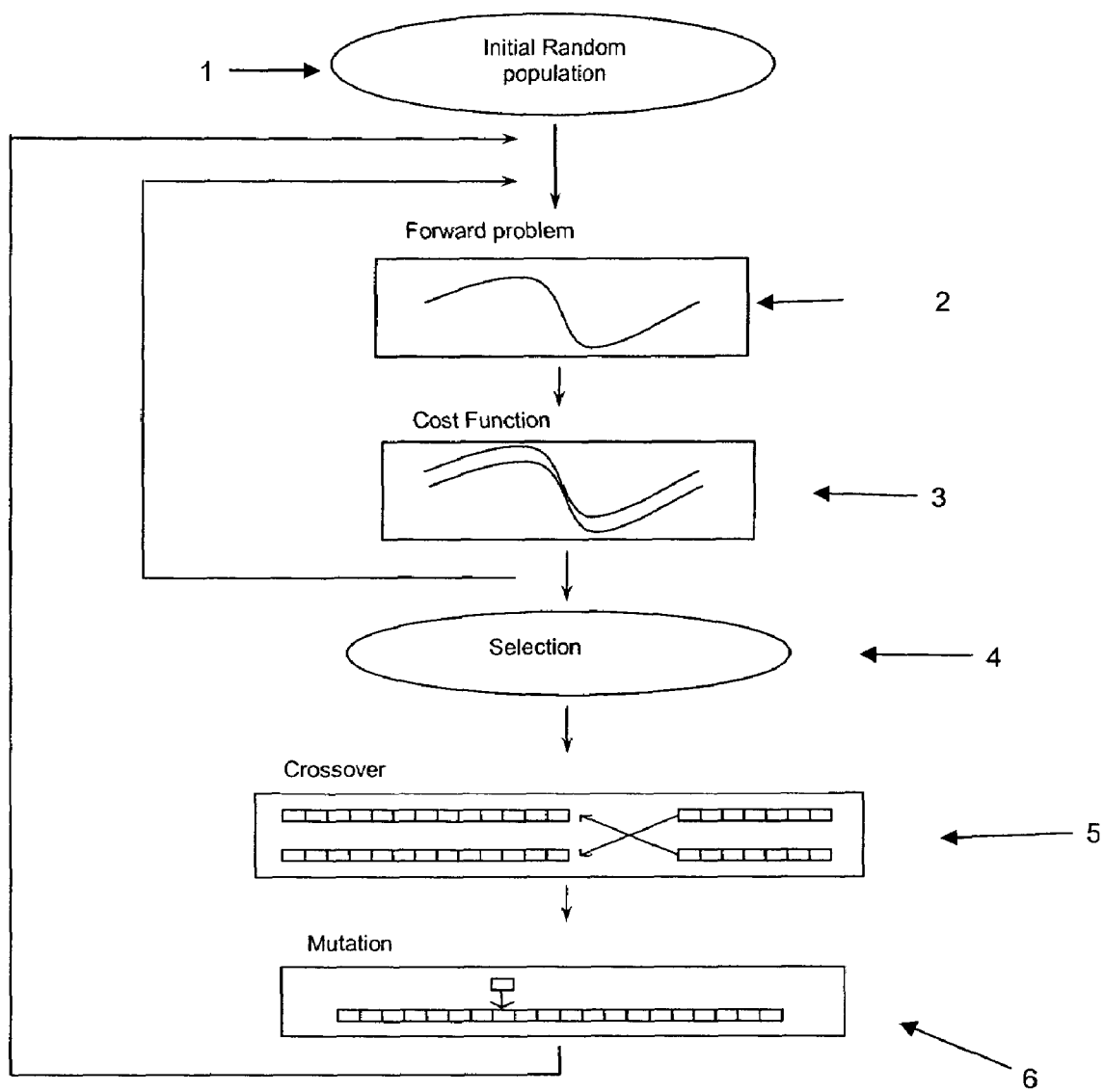
FIG. 7 is a schematic drawing illustrating the method of genetic algorithms employed in the present invention.

The flow diagram of FIG. 7 summarizes the process utilized to apply an inversion scheme based on genetic algorithms, similar to the one described by Rodriguez-Zúñiga et al. (1996) and Ortiz-Aleman et al. (2002, 2003) for the inversion of underground elastic parameters from surface inclination data and for the inversion of aeromagnetic data, respectively. The basic steps of the process are briefly described next, with reference to FIG. 7.

Discretization

In the block (1) of FIG. 7, the parameters are represented by the vector of unknowns s, which represents the unknown permittivity distribution. The cost function, which determines the fit between the observed data and the synthetic response of a given model, is denoted by $E(\in)$. The parameter coding is done taking into account the required search range within the model space, as well as the desired resolution (Stoffa y Sen, 1991). In this way, the range is defined for each parameter defining a couple of bounds $a_i$ and $b_i$, that is to say, $a_i < \in_i < b_i$. The resolution is controlled with the discretization interval $d_i$, defined as $$d_i = \frac{(b_i - a_i)}{N_i} \quad (16)$$

where $N_i$ is the number of possible values for the parameter during the process (Sambridge and Drijkoningen, 1992). The allowed models, $\in$, defined by the set of parameters $\in_i$, are restricted to the domain of values $$\in_i = a_i + j d_i \text{ for } j=0, \ldots, N_i \quad (17)$$

Initial Population

Also in block (1) of FIG. 7, from random combinations of the parameters, an initial population of models is constructed, whose dimension depends on the particular problem to be solved. Each combination translates into a set of integer indexes, defined by equation (17). Said integer values, which establish the particular value for each model parameter, are later codified as binary chains called chromosomes. Said chains are made up of consecutive groups of bits, called genes, that represent the value of the different parameters $\in_i$.

The models that form the population in later generations are created applying the three essential evolutionary mechanisms: selection, crossover and mutation.

Forward Problem and Evaluation of the Cost Function

The forward problem in block (2) of FIG. 7 consists in calculating the theoretical or synthetic response for each model during the iterative process. Said response is then compared in block (3) of FIG. 7 with the observations or data using some measure of similarity known as cost function. The criterion utilized in this work is the $L_2$ norm already defined in equation (14), albeit there can be others. The norm chosen to evaluate the fit must take into account the form and complexity of the observed and calculated curves.

Selection

In block (4) of FIG. 7, starting from a population of Q individuals and their respective cost functions $E(\in k)$ (k=1, ..., Q), a ('cumulative') probability of selection $P(\in k)$ is determined that will depend on its degree of fitness.

One formula that can be used to determine the cumulative probability of selection is $$P(\varepsilon_k) = P(\varepsilon_{k-1}) + \frac{E_{max} - E(\varepsilon_k)}{Q(E_{max} - E_{avr})} \quad (18)$$

where $E_{max}$ and $E_{avr}$ are maximum and average cost functions of the generation, respectively, and Q is the number of individuals in the population. Next, a biased roulette procedure (Goldberg, 1989) is used to select a new population of models. Q random numbers $r_k$ between cero and one are generated. If $P(\in_{k-1})<r_k<P(\in_k)$, then $\in_k$ is selected to be part of the new population. This means that in the new population there may be some 'twin' models. Additionally, 'clones' of the best models can be added to the base population of Q models. Said 'clones' will not suffer crossover nor mutation, in order to ensure that these desirable models are not lost when going through those processes, which are of a random nature.

Alternatively, the selection probability can be determined as (Sambridge y Drijkoningen, 1992)

$$P(\in_k)=a-bE(\in_k) \quad (19)$$

which describes a linear probability distribution, and $$P(\in_k)=Ae^{-BE(\in_k)} \quad (20)$$

which corresponds to an exponential distribution. The values that are often given to the constants a, b, A y B are as follows $$b = Q^{-1}(E_{max} - E_{avr})^{-1}, a \geq bE_{max}$$

$$B = (E_\sigma)^{-1}, A = \left[\sum_k e^{-BE(\varepsilon_k)}\right]^{-1},$$

where $E_{max}$, $E_{avr}$ and $E_\sigma$ are the maximum and average cost functions, and the standard deviation of all the misfits of the initial population, respectively.

Stoffa and Sen (1991) propose a selection criterion based on an update probability. The criterion consists in comparing the misfit of each model from the current generation with that of a model from the previous generation, chosen at random. If the misfit of the current model is smaller, then it is saved. If not, a value $P_u$ is considered that establishes the probability of substituting the current model for the previous one. The procedure controls the influence of the misfit of previous generations on the current population. The value suggested by Stoffa and Sen (1991) for the substitution probability $P_u$ is 90%.

Crossover

The new models are produced in block (5) of FIG. 7 from a parent generation of Q models. Q/2 pairs are formed randomly. Each pair is potentially able to mate. In order to determine which pairs are to be crossed over, each one is assigned a random number between cero and one. If said number is smaller that the crossover probability $P_c$, then the corresponding pair are crossed over. If not, both members of the pair are kept unchanged in the next generation.

Figure 8:
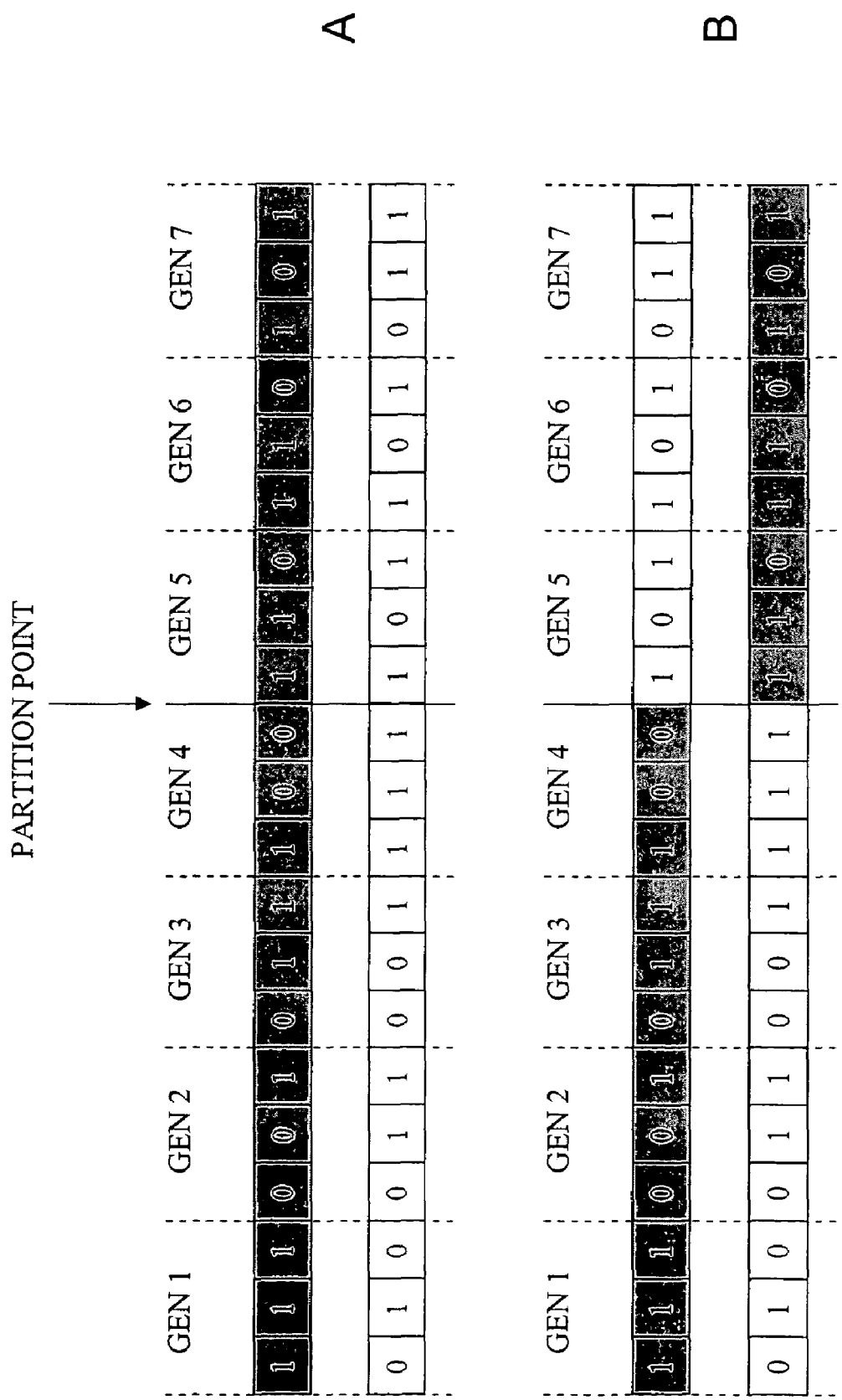
FIG. 8 shows schematically the process of crossover used in genetic algorithms employed in the present invention.

The crossover mechanism is based on choosing randomly the position of a gene for both chains. The chains are broken at that point to interchange information between them, as can be seen in FIG. 8, where is shown in (A) the partition of the chromosomes into four gamets, and in (B) the exchange and union of two gametes to form two cigots. The purpose of crossing over two different chains is to explore new regions of the solution domain, where the absolute minimum might lie. In the normal crossover process, the mated pairs have two children, and the population of models is automatically maintained in Q individuals. Alternatively, it can be considered that the couples have only one child, in which case the population must be completed with randomly generated models until it reaches Q individuals.

Mutation

Figure 9:
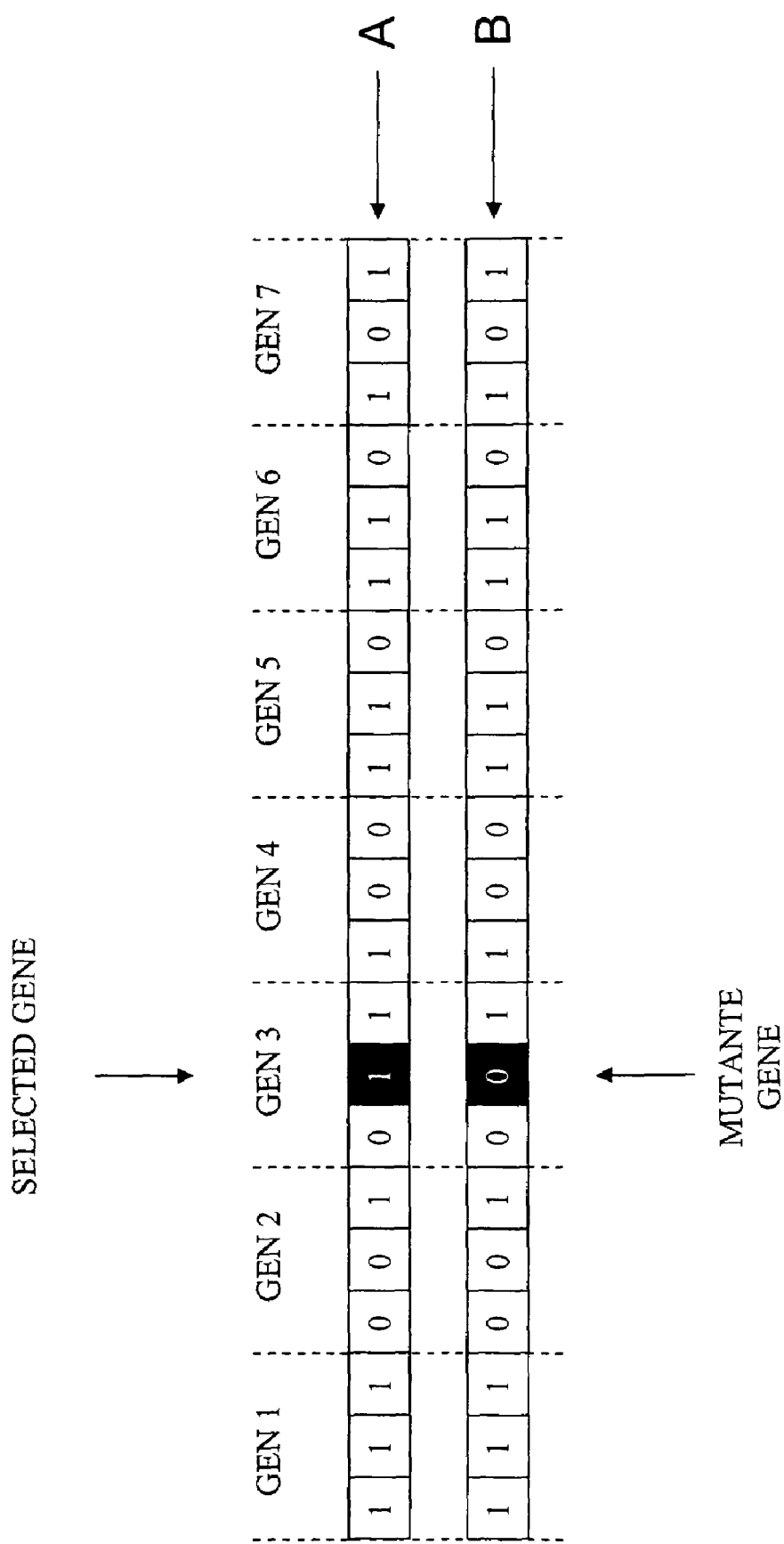
FIG. 9 shows schematically the process of mutations used in genetic algorithms employed in the present invention.

Mutation, like the sexual reproduction (or crossover), contributes to the genetic diversity of a population. Mutation allows the search to prosper when it is confined in the vicinity of a local minimum. The mutation is done in block (6) of FIG. 7 by inverting a bit chosen at random within the binary chain (chromosome). The number of models to which the process of mutation is applied, as in the crossover, depends on a parameter called probability of mutation, denoted by $P_m$. This mechanism prevents the premature convergence of the method, when the population is too homogeneous and incapable to continue the evolutionary process. In FIG. 9 an arbitrary chain is represented and the mutation of a random bit is exemplified, the original chromosome is shown in (A) and the mutated one is shown in (B).

An alternative to define the probability of mutation $P_m$ was proposed by Yamanaka and Ishida (1996). It consists in determining the level of homogeneity of the individuals in every generation through the calculation of an average variation coefficient $\gamma$, for each parameter, using the formula $$\gamma = \frac{1}{p}\sum_{i=1}^{P}\left(\frac{\sigma_i}{\overline{\varepsilon}_i}\right) \quad (21)$$

where p is the number of parameters, $\overline{\in}_i$ is the average of the i-th parameter, and $\sigma_i$ is the standard deviation. Below, $P_m$ is defined as a function of $\gamma$ $$P_m = \begin{cases} P_{ini} & \text{para } \gamma > 0.1 \\ 0.1 & \text{para } 0.02 < \gamma < 0.1 \\ 0.2 & \text{para } \gamma < 0.02 \end{cases} \quad (22)$$

where $P_{ini}$ is the initial probability of mutation.

With mutation concludes the sequence of operations that define a genetic algorithm. Said sequence is repeated until some pre-established tolerance is satisfied.

Figure 10:
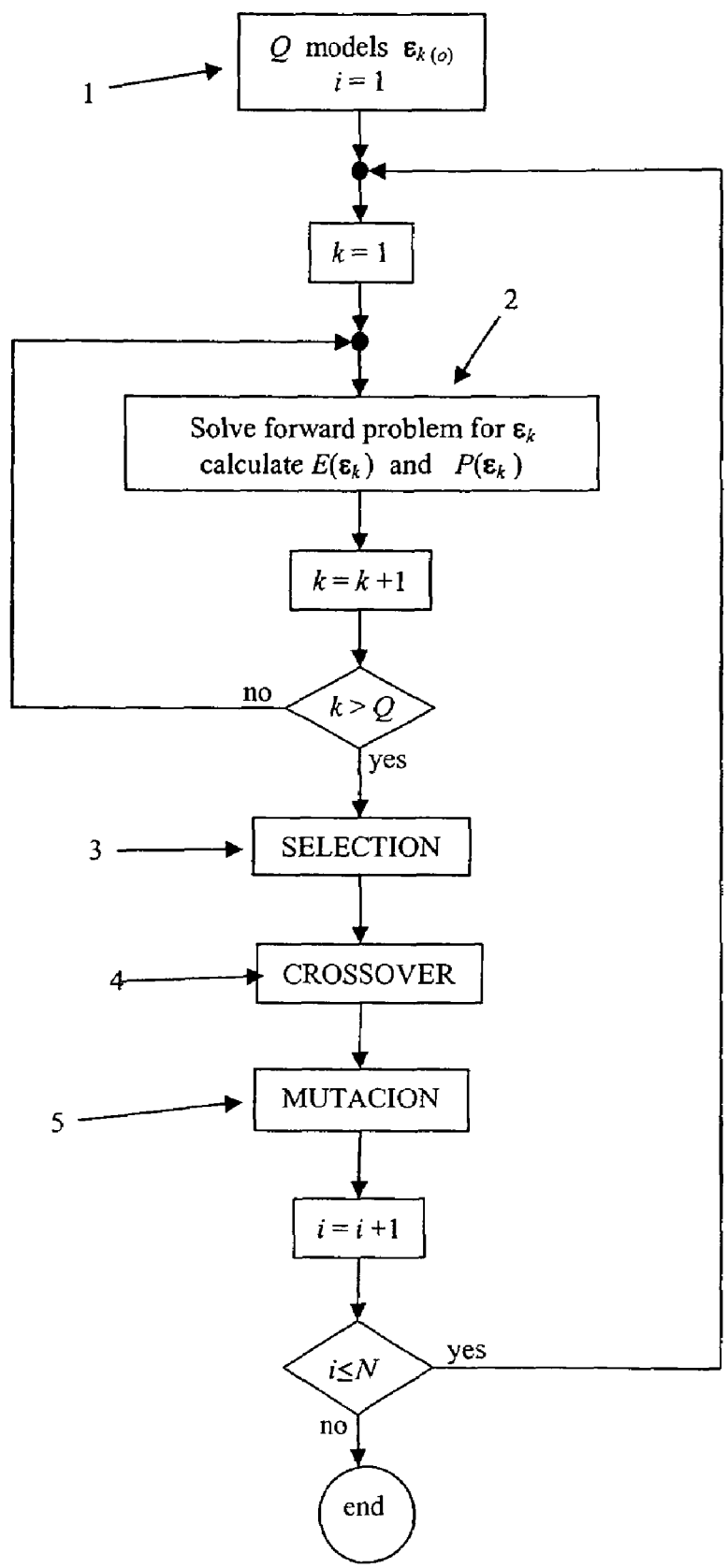
FIG. 10 shows the flow diagram of one possible implementation of the method of genetic algorithms employed in the present invention.

As an example, one possible specific embodiment, albeit not the only one, of the method of genetic algorithms, is presented in FIG. 10. In block (1), the method starts with a population of Q randomly generated models, each one representing a permittivity distribution. At the same time, also in block (1) the iteration counter i is initialized. Next, the model counter k is initialized and a cycle begins through which, for each one of the Q models, the forward problem is solved and the misfit function $E(\in_k)$ as well as the cumulative probability of selection $P(\in_k)$ are calculated in block (2). After that, selection of the models with lower E is performed in block (3) according to the value of $P(\in_k)$ and applying the process of biased roulette previously described. Then follows model crossover in block (4). In said block (4), Q/2 pairs of models are formed at random, which are then selectively crossed over based on the value of $P_c$, producing only one child per pair. Also in block (4), the pairs not crossed over remain (both members) unchanged and the population is completed to Q individuals with new random models. Finally, in block (5) the average variation coefficient $\gamma$ and the mutation probability $P_m$ are calculated, and then model mutation is carried out according to the description already given in previous paragraphs. The whole previous procedure is repeated continuously, increasing i by one on every iteration. The algorithm ends when a pre-set number of iterations N is reached or if the misfit function is sufficiently small.

Formulation of the Forward Problem

The forward problem consists in calculating the mutual capacitances $c_{ij}$, $i \neq j$, that result from the presence of a permittivity distribution E inside the sensor. Both methods, simulated annealing and genetic algorithms, require the repeated solution of the forward problem. Because of that, it is important to have a suitable method to solve said problem, that achieves a reasonable balance between accuracy (or precision) and speed. In the context of this invention, the forward problem can be solved using an optimized routine developed by the authors based on the finite-volume method, which will be described briefly. This routine is more efficient than those reported so far in the literature (Yang y Peng, 2003) for it is comparable in its precision with implementations based on the finite-element method using meshes with 9,000 triangular elements. The execution speed is higher than that of finite-element and finite-difference methods. The routine is written in Fortran 90 and is totally portable (it has been tested on PC-type computers, MS-Windows and Linux based PC clusters, SUN and ALPHA workstations, and CRAY supercomputers). The routine can be extended to the three-dimensional case without any major modifications and is easily parallelizable.

The forward problem is solved using the finite-volume method in a cylindrical configuration. In this way, the intermediate solutions in the center of the disc (which are a problem in the finite-difference method) are eliminated and the mesh refinement becomes more flexible compared with finite-element methods. Equation (7), repeated below, is solved $$\nabla \cdot \in (x,y) \nabla \phi^k = 0$$

where $\in$ is the permittivity and $\phi^k$ is the electrostatic potential generated when electrode k is the source (or excitation). The equation is subject to the boundary conditions (a) $\phi^k = V$ volts on the source electrode and (b) $\phi^k = 0$ on the detection electrodes and on the outer screen.

Defining the radial and angular coordinates as r and $\theta$, and using the finite-volume method, the discrete equation is formulated in conservative form for each cell $\Omega_{ij}$ as $$\int_{\Omega_{ij}} \nabla \cdot (\in \nabla \phi^k) d\Omega_{ij} = 0 \text{ for } i=1, \ldots, N_r \text{ and } j=1, \ldots, N_\theta \quad (23)$$

where i and j refer to the discretization in r and $\theta$, respectively, and $N_r$ and $N_\theta$ are the number of sections into which the radius and the circumference are divided, respectively.

Applying Gauss's theorem in polar coordinated, the discrete equations can be written as $$\int_{\Gamma_{ij}} \in \nabla \phi^k \cdot d\Gamma_{ij} = 0 \quad (24)$$

where $\Gamma_{ij}$ is the boundary of the finite volume cell $\Omega_{ij}$. The boundary $\Gamma_{ij}$ is defined by $\Gamma_W$ and $\Gamma_E$ along the radial coordinates, and by $\Gamma_N$ and $\Gamma_S$ along the angular coordinates. Equation (24) can be expressed as the sum of the fluxes through the faces $\Gamma_N$, $\Gamma_S$, $\Gamma_E$ and $\Gamma_W$ $$\sum_l \left( \int_{\Gamma_l} \in \nabla \phi^k \cdot n_l d\Gamma_l \right) = \begin{pmatrix} \left( \frac{\in}{r} \frac{\partial \phi^k}{\partial \theta} \Delta r \right)\bigg|_{(i+\frac{1}{2}),j} - \left( \frac{\in}{r} \frac{\partial \phi^k}{\partial \theta} \Delta r \right)\bigg|_{(i-\frac{1}{2}),j} + \\ \left( \in \frac{\partial \phi^k}{\partial \theta} r\Delta\theta \right)\bigg|_{i,(j+\frac{1}{2})} - \left( \in \frac{\partial \phi^k}{\partial \theta} r\Delta\theta \right)\bigg|_{i,(j-\frac{1}{2})} \end{pmatrix} \quad (25)$$

From (25), the term corresponding to the fluxes at cero radius vanishes and the problem is equivalent to solving the equations in the proximity of the center on triangles that have a vertex on the center. Then, the discrete system of equations for the forward problem is well posed. The complete system is similar to a Laplacian system of equations, and a diagonal banded system that includes the periodic boundary conditions imposed by the problem geometry must be solved. The corresponding matrix is positive definite and non-symmetric, characteristics that can be exploited when selecting the specific optimum solution methods.

Finally, the mutual capacitances are calculated by integrating the potential gradients along a curve surrounding the electrodes, according to equation (6), which is repeated below $$c_{ij} = \frac{q_i}{v_k} = -\frac{\in_0}{V} \oint_{\Gamma_k} (\in \nabla \phi^k) \cdot dl = -\frac{\in_0}{V} \oint_{\Gamma_k} \in \frac{\partial \phi^k}{\partial n} dl$$

where $\in_o$ is the permittivity of free space ($8.854 \times 10^{-12}$ farads per meter), $\Gamma_i$ is a closed curve surrounding electrode i, dl is a normal vector representing an element of the curve $\Gamma_i$, dl is an element of length of that curve and $\phi^k$ is the electrostatic potential produced in the sensor when applying a voltage of V volts to electrode k (source or excitation) and 0 volts to all others (detection electrodes). The integration is done using a trapezoidal rule and the potential gradients are calculated to the fourth order.

During the procedure for reconstructing a permittivity image using simulated annealing, it is necessary to solve the forward problem and find the electric potential repeatedly for relatively similar successive permittivity distributions, while the method converges towards the final solution. Since the potential corresponding to said successive distributions changes relatively little, it is possible to accelerate the whole process if an iterative method is used to solve the forward problem, taking as the first guess for the potential the solution potential corresponding to the previous permittivity configuration. Because the initial guess for the potential will be quite close to the solution, said iterative method will converge in a few iterations, rapidly achieving an acceptable accuracy.

EXEMPLARY EMBODIMENTS

With the purpose of evaluating the performance of the image reconstruction methods described previously, a set of synthetic ECT data were calculated using the forward problem routine. In order to emulate the main sources of uncertainty in the data produced by a measuring instrument operating in real working conditions (i.e., the random errors inherent to the process of measuring any physical quantity and the errors caused by the limited precision of the measuring instrument), the calculation of the synthetic capacitances for the ideal model were evaluated with a numeric precision of the order of $10^{-11}$ in the iterative method used in the forward problem for the calculation of the potential. To emulate the (systematic) imprecision associated with the ECT sensor, during the inversion process (i.e., the estimation of the electrical permittivity distribution inside the pipe) a considerably smaller precision ($10^{-5}$) was used in the calculation of the potentials in the forward problem.

The interpretation of potential-field data without any restriction can be of very little practical interest due to the great ambiguity present between the observations and the estimated solutions. The non-uniqueness in the potential-field problems arises mainly from two sources: the first is the inherent ambiguity caused by physics of the problem that permits the existence of many solutions that reproduce the anomaly in the potential field; the second results from the use of a finite number of data that are contaminated with errors and that may not contain enough information to construct a unique solution to the problem. The strategies that allow overcoming this non-uniqueness consist in the incorporation of sufficient a-priori information to constrain the resulting solutions to a region in the parameter space that is considered physically reasonable (Pilkington, 1997). In the particular case of electrical capacitance tomography, there is information about the typical values of the electrical permittivity for gas, oil and water. The knowledge of these values, as well as the significant contrast between the properties of gas and oil, allow the application of the inversion techniques discussed here to ECT data for two-phase flows contaminated with relative errors of up to 2% (this being the maximum error produced by the data acquisition systems normally employed in ECT). Additionally, if there is a precise statistical estimation of the data uncertainty, then it is possible to construct a model that considers the uncertainties in the data and in the parameter estimations, using the scheme proposed by several authors for the inversion of potential-field data (for example, Sen and Stoffa, 1995).

The synthetic capacitances were calculated for three typical permittivity distributions using the forward problem subroutine based on finite volumes. A 12-electrode ECT sensor was simulated and the capacitance values for all possible electrode-pair combinations were calculated. Those were the simulated data. A two-component distribution was considered with a material with a low permittivity of 1 (gas) and another with a high permittivity of 2.5 (oil). Tests were carried out with noise-free data and with data contaminated with random errors of up to 1%. The algorithm is written in Fortran 90 and runs on a 1.7-gigahertz Pentium 4 computer with 512 megabytes of RAM memory. The tests were done using a mesh having 120×60 elements in order to reduce the inversion time (~30 minutes for 60,000 iterations), but the results are valid for larger dimensions. The validity of these simulations was corroborated with experimental laboratory results obtained using physical models and a real electrical capacitance tomography system.

Figure 11:
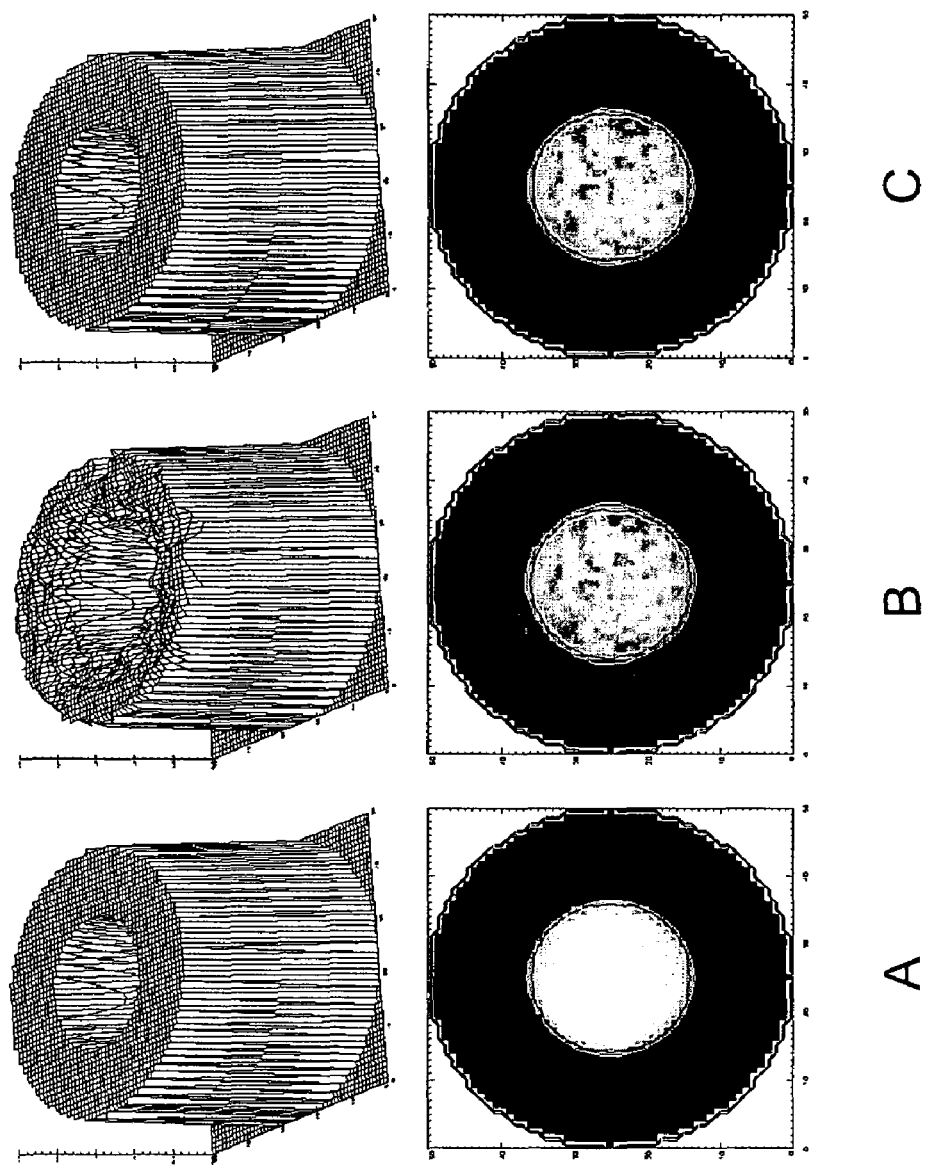
FIG. 11 shows the results obtained by reconstructing images of a simulated gas-oil annular flow, using the simulated annealing method in the present invention.
Figure 12:
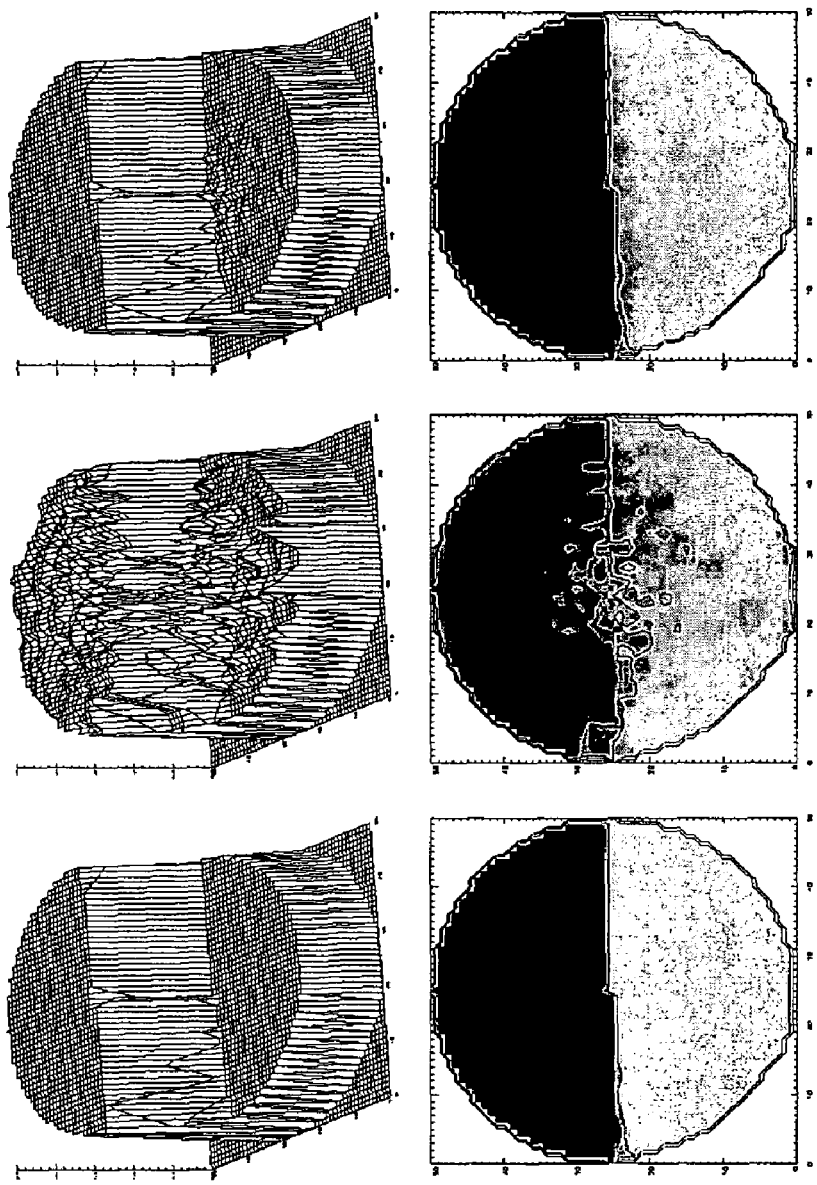
FIG. 12 shows the results obtained by reconstructing images of a simulated gas-oil stratified flow, using the simulated annealing method in the present invention.

After a suitable parameterization, both simulated annealing and genetic algorithms yielded very similar results for the three cases studied. The quality of the reconstructed permittivity images depends mainly on the number of iterations of the method, as it happens in many other applications (for example, Ortiz Aleman et al., 1999, 2001, 2002, 2003; Cruz-Atienza, 1999). In FIG. 11, the reconstructions for a simplified annular flow (A) are presented, after 30,000 (B) and 60,000 (C) calculations of the direct problem (i.e., iterations of the inversion method). In FIGS. 12 and 13, similar illustrations are shown for a stratified flow and a bubbly flow, showing in (A) the ideal image, in (B) the reconstructed image after 30,000 iterations, and in (C) the reconstructed image after 60,000 iterations. In all cases shown in the figures, the simulated annealing method was used starting from an initial homogeneous permittivity distribution. These results show clearly that the reconstructed images closely resemble the 'true' ones. The accuracy of these reconstructions is considerably better than those reported so far in the literature (Yang and Peng, 2003). Albeit the methods of this invention do not require that the initial guess for the permittivity distribution be close to the solution in order to converge, it is possible to speed up the process a little if the image resulting from a simple direct method such as LPB is used as the first guess.

What is claimed is:

1. An image reconstruction method from electrical capacitance tomography data comprising: (a) obtaining the measurement electrical capacitance tomography data by using a recording sensor formed by an array of electrodes located on the perimeter of an oil-pipe, well or tank; (b) processing said measurement data using the Method of Simulated Annealing for the estimation of an electrical permittivity distribution image; and (c) displaying said processed image on a display device in order to visualize multiphase oil-flows through a cross section of a pipe, well or tank.

2. A method according to claim 1, wherein the measurement data are collected on the perimeter of a region such as the inside of an oil-pipeline, well or tank.

3. A method according to claim 2, wherein said are the electrical capacitance values recorded between the electrodes of a sensor, which is formed by a plurality of said electrodes placed around the perimeter of the region (pipeline, well, tank).

4. A method according to claim 3, wherein said sensor is formed by a pipe made of an electrically insulating material, on whose outer wall an array of rectangular metallic electrodes is placed.

5. A method according to claim 3, wherein the sensor contains a multiphase or multicomponent flow, and images that show the distribution of the phases or components, such as gases or/and liquids, are obtained in accordance to what is said in the background of the invention.

6. A method according to claim 2, wherein said permittivity image is formed by a finite number of sub-regions or pixels in the oil-flow viewing, which number depends on the desired resolution permittivity image resolution.

7. A method according to claim 1, wherein said estimated image represents the spatial distribution of the electrical permittivity in a cross sectional region of an oil-pipeline, well, or tank, which reflects the spatial distribution of the materials or substances, such as gases and/or liquids, that are flowing through this region (pipeline, well, tank).

8. A method according to claim 1, wherein a cost function associated to the energy of the system is iteratively minimized with respect to E (the vector of the permittivity values in each pixel of the image), said cost function being of the form:

$$E_k = L_{2(k)} = \frac{\sum_{i=1}^{m}[c_i^{meas} - c_i^{calc}(\varepsilon_k)]^2}{\sum_{i=1}^{m}[c_i^{meas}]^2} \quad (i = 1, \ldots, m)$$

where $c_i^{meas}$ are the m measured mutual capacitances and $c_i^{calc}(\in_k)$ are the ones calculated by solving the forward problem for a given permittivity distribution $\in_k$.

9. A method according to claim 8, wherein the Metropolis criterion is used to do the minimization.

10. A method according to claim 9, wherein in the minimization process it is used, as the initial guess for the permittivity distribution, E, both a homogeneous distribution and the distribution that results from applying the linear back-projection (LBP) method to the measurement data.

11. A method according to claim 8, wherein the computation of the calculated capacitances $c_i^{calc}(\in_k)$ known as the forward problem, is carried out by means of the finite-volume method.

12. A method according to claim 11, wherein for the solution of the system of equations that results from solving the forward problem $c_i^{calc}(\in_k)$, iterative methods that rapidly converge are used, by employing as initial estimation of the electrostatic potential the result of the forward problem solution obtained in the previous iteration of the inverse problem.

13. A method according to claim 1, wherein the method of genetic algorithms is used as an alternative electrical permittivity image estimation method.

14. A method according to claim 13, wherein, starting from an initial population of Q permittivity models $\in_{k(o)}$ (k=1, . . . , Q), evolutionary mechanisms such as selection, crossover and mutation are applied in order to obtain new populations.

15. A method according to claim 14, wherein individuals $\in_k$ are characterized by having a small cost (or misfit) function, which is given by $$E_k = L_{2(k)} = \frac{\sum_{i=1}^{m}[c_i^{meas} - c_i^{calc}(\varepsilon_k)]^2}{\sum_{i=1}^{m}[c_i^{meas}]^2} \quad (i = 1, \ldots, m)$$

where $c_i^{meas}$ are the m measured mutual capacitances and $c_i^{calc}(\in_k)$ are the calculated ones by solving the forward problem for a given model or permittivity distribution $\in_k$.

16. A method according to claim 14, wherein the accumulated probability of selection for a particular model $\in_k$ is given by $$P(\varepsilon_k) = P(\varepsilon_{k-1}) + \frac{E_{max} - E(\varepsilon_k)}{Q(E_{max} - E_{avr})}$$

where $E_{max}$, and $E_{avr}$ are maximum and average cost functions of the generation, respectively, and Q is the number of individuals in the population.

17. A method according to claim 16, wherein a biased roulette procedure can be used to decide which models are selected on each iteration of the method.

18. A method according to claim 17, wherein crossover and mutation of models are carried out randomly according to the probabilities of crossover and mutation, $P_c$ y $P_m$.

19. A method according to claim 18, wherein the probability of mutation $P_m$ is determined using the average variation coefficient γ, given by $$\gamma = \frac{1}{p}\sum_{i=1}^{P}\left(\frac{\sigma_i}{\overline{\varepsilon}_i}\right)$$

where p is the number of parameters, $\overline{\in}_i$ is the average of the i-th parameter, and $\sigma_i$ is the standard deviation.

20. A method according to claim 18, wherein $P_m$ is defined as a function of γ, that is:

$$P_m = \begin{cases} P_{ini} & para \quad \gamma > 0.1 \\ 0.1 & para \quad 0.02 < \gamma < 0.1 \\ 0.2 & para \quad \gamma < 0.02 \end{cases}$$

where $P_{ini}$ is the initial probability of mutation.

21. A method according to claim 14, wherein the calculation of $c_i^{calc}(\in_k)$, known as the forward problem, is performed by means of the finite-volume method.

* * * * *